(12) United States Patent
Zhong et al.

(10) Patent No.: US 12,232,857 B2
(45) Date of Patent: Feb. 25, 2025

(54) DEVICES, SYSTEMS, AND METHODS FOR NOISE REDUCTION

(71) Applicant: SHANGHAI UNITED IMAGING HEALTHCARE CO., LTD., Shanghai (CN)

(72) Inventors: Rong Zhong, Shanghai (CN); Xiangming Hou, Shanghai (CN); Wentao Wu, Shanghai (CN); Xinyue Zhang, Shanghai (CN); Shuangyue Zhang, Shanghai (CN); Tuoyu Cao, Shanghai (CN); Lingzhi Hu, Houston, TX (US); Guobin Li, Shanghai (CN); Weidong Wang, Shanghai (CN); Junyu Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 226 days.

(21) Appl. No.: 17/930,710

(22) Filed: Sep. 8, 2022

(65) Prior Publication Data

US 2023/0076542 A1 Mar. 9, 2023

(30) Foreign Application Priority Data

Sep. 8, 2021 (CN) .......................... 202122168874.6
Mar. 30, 2022 (CN) .......................... 202220717480.3

(51) Int. Cl.
*A61B 5/055* (2006.01)
*G01R 33/385* (2006.01)
(Continued)

(52) U.S. Cl.
CPC .......... *A61B 5/055* (2013.01); *G01R 33/3854* (2013.01); *H04R 17/00* (2013.01);
(Continued)

(58) Field of Classification Search
CPC .... A61B 5/055; G01R 33/3854; H04R 17/00; H04R 1/028; H04R 2217/01;
(Continued)

(56) References Cited

U.S. PATENT DOCUMENTS 5,427,102 A * 6/1995 Shimode .................. H04R 3/00
324/318
5,548,653 A * 8/1996 Pla .................... G10K 11/17854
381/71.11
(Continued)

FOREIGN PATENT DOCUMENTS

CN 106303885 A 1/2017

OTHER PUBLICATIONS

Zhang, Wenqing et al., Experimental Research on Active Noise Reduction Based on Secondary Sound Source Layout Optimization, Machinery & Electronics, 35(6): 3-7+11, 2017.

*Primary Examiner* — Daniel R Sellers
(74) *Attorney, Agent, or Firm* — METIS IP LLC

(57) ABSTRACT

The present disclosure provides a noise reduction device. The noise reduction device may include a noise receiving component, a noise reduction component, a processing component, and a housing. The noise receiving component may be configured to receive acoustic noise information of a scanning environment where a medical device is located. The processing component may be configured to control the noise reduction component to generate sound information matching the acoustic noise information received by the noise receiving component. The housing may be configured to support the noise receiving component and the noise reduction component.

20 Claims, 13 Drawing Sheets

(51) Int. Cl.
*G10K 11/178* (2006.01)
*H04R 1/02* (2006.01)
*H04R 17/00* (2006.01)

(52) U.S. Cl.
CPC ... *A61M 2205/42* (2013.01); *G10K 11/17857* (2018.01); *G10K 2210/116* (2013.01); *G10K 2210/1161* (2013.01); *H04R 1/028* (2013.01); *H04R 2217/01* (2013.01)

(58) Field of Classification Search
CPC ....... G10K 11/17857; G10K 2210/116; G10K 2210/1161; A61M 2205/42
See application file for complete search history.

(56) References Cited

U.S. PATENT DOCUMENTS

| | | | | |
|---|---|---|---|---|
| 5,577,504 | A * | 11/1996 | Salloway | G01R 33/3854 324/318 |
| 6,954,666 | B2 * | 10/2005 | Bechtold | G10K 11/17885 600/410 |
| 2001/0033124 | A1 * | 10/2001 | Norris | G10K 11/025 181/177 |
| 2005/0089176 | A1 * | 4/2005 | Norris | H04R 17/00 381/79 |
| 2005/0248346 | A1 * | 11/2005 | Sellers | G01R 33/3854 324/318 |
| 2007/0090840 | A1 * | 4/2007 | Chmielewski | G01R 33/34046 324/318 |
| 2015/0100310 | A1 * | 4/2015 | Cha | G10K 11/17823 324/318 |
| 2016/0119704 | A1 * | 4/2016 | Brown | G10L 21/0272 381/375 |
| 2016/0199241 | A1 * | 7/2016 | Rapoport | G10K 11/162 600/22 |
| 2017/0119320 | A1 * | 5/2017 | Ueda | A61B 5/11 |
| 2017/0332165 | A1 * | 11/2017 | Goto | H04R 1/24 |
| 2021/0161498 | A1 * | 6/2021 | Hu | G01R 33/3854 |

* cited by examiner

300

DEVICES, SYSTEMS, AND METHODS FOR NOISE REDUCTION

CROSS-REFERENCE TO RELATED APPLICATIONS

This application claims priority to Chinese Patent Application No. 202122168874.6, filed on Sep. 8, 2021, and Chinese Patent Application No. 202220717480.3, filed on Mar. 30, 2022, the contents of each of which are incorporated herein by reference.

TECHNICAL FIELD

The present disclosure generally relates to medical devices, and more particularly, to devices, systems, and methods for noise reduction for medical devices.

BACKGROUND

In recent years, medical devices have been widely used in the diagnosis and treatment. However, the medical devices usually produce strong vibrations and large noise during use, which reduce comfort of patients and/or users. For example, when a superconducting magnetic resonance system is used to scan a patient, noise is generated due to switching of a gradient field and transmitted to a scanning chamber where the patient is located through air or mechanical vibrations of components of the superconducting magnetic resonance system, which reduces the comfort of the patient during the scan. Therefore, it is desirable to provide devices, systems, and methods for noise reduction for the medical devices.

SUMMARY

In one aspect of the present disclosure, a device for noise reduction is provided. The noise reduction device may include a noise receiving component, a noise reduction component, a processing component, and a housing. The noise receiving component may be configured to receive acoustic noise information of a scanning environment where a medical device is located. The processing component may be configured to control the noise reduction component to generate sound information matching the acoustic noise information received by the noise receiving component. The housing may be configured to support the noise receiving component and the noise reduction component.

In some embodiments, the noise receiving component may be located on an inner surface or an outer surface of the housing, and the noise reduction component may be located on the outer surface of the housing.

In some embodiments, the noise reduction component may include a flat panel speaker or a curved speaker.

In some embodiments, a parameter of the noise reduction component may be designed according to noise reduction requirement. The parameter may include at least one of a shape, a length, a width, a radius, or a thickness of the noise reduction component.

In some embodiments, the noise reduction component may include at least two noise reduction units. The at least two noise reduction units may be disposed on two opposite sides of the housing.

In some embodiments, parameters of the at least two noise reduction units are at least partially different, the parameter of the noise reduction unit including at least one of a shape, a length, a width, a radius, or a thickness.

In some embodiments, at least one through hole may be disposed at a position of the housing where the noise reduction component is located.

In some embodiments, the at least one through hole may be disposed in rows and columns.

In some embodiments, a size of the at least one through hole may be within a preset range.

In some embodiments, the noise reduction device may further include a support component configured to support the noise reduction component.

In some embodiments, the support component may include a support frame and a vibration isolation structure. The vibration isolation structure may be located in the support frame or located between the support frame and the noise reduction component.

In some embodiments, the support frame may include a frame body and a side edge. The side edge may be disposed on the frame body and protrudes from the frame body.

In some embodiments, the noise reduction device may further include a fixing structure fixedly connected to the side edge.

In some embodiments, the noise reduction device may further include a second housing located outside the housing. The second housing and the housing may form an enclosed structure.

In another aspect of the present disclosure, a device for noise reduction disposed on a head coil assembly is provided. The noise reduction device may include a noise receiving component, a first housing, a second housing, a noise reduction component, and a processing component. The noise receiving component may be configured to receive acoustic noise information of a scanning environment where a medical device is located. The second housing and the first housing may form an accommodation chamber. The noise reduction component may be located on the first housing and/or the second housing. The processing component may be configured to control the noise reduction component to generate sound information matching the acoustic noise information received by the noise receiving component.

In still another aspect of the present disclosure, a device for noise reduction is provided. The noise reduction device may include a first noise receiving component located on an inner side wall of a chamber, a first noise reduction component located on an outer surface of a housing, a second noise receiving component located on an inner surface of the housing, a second noise reduction component located on the inner surface of the housing, and a processing component. The processing component may be configured to control the first noise reduction component to generate first sound information matching first acoustic noise information received by the first noise receiving component and/or control the second noise reduction component to generate second sound information matching second acoustic noise information received by the second noise receiving component. The first acoustic noise information and the second acoustic noise information may be from a scanning environment where a medical device is located.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
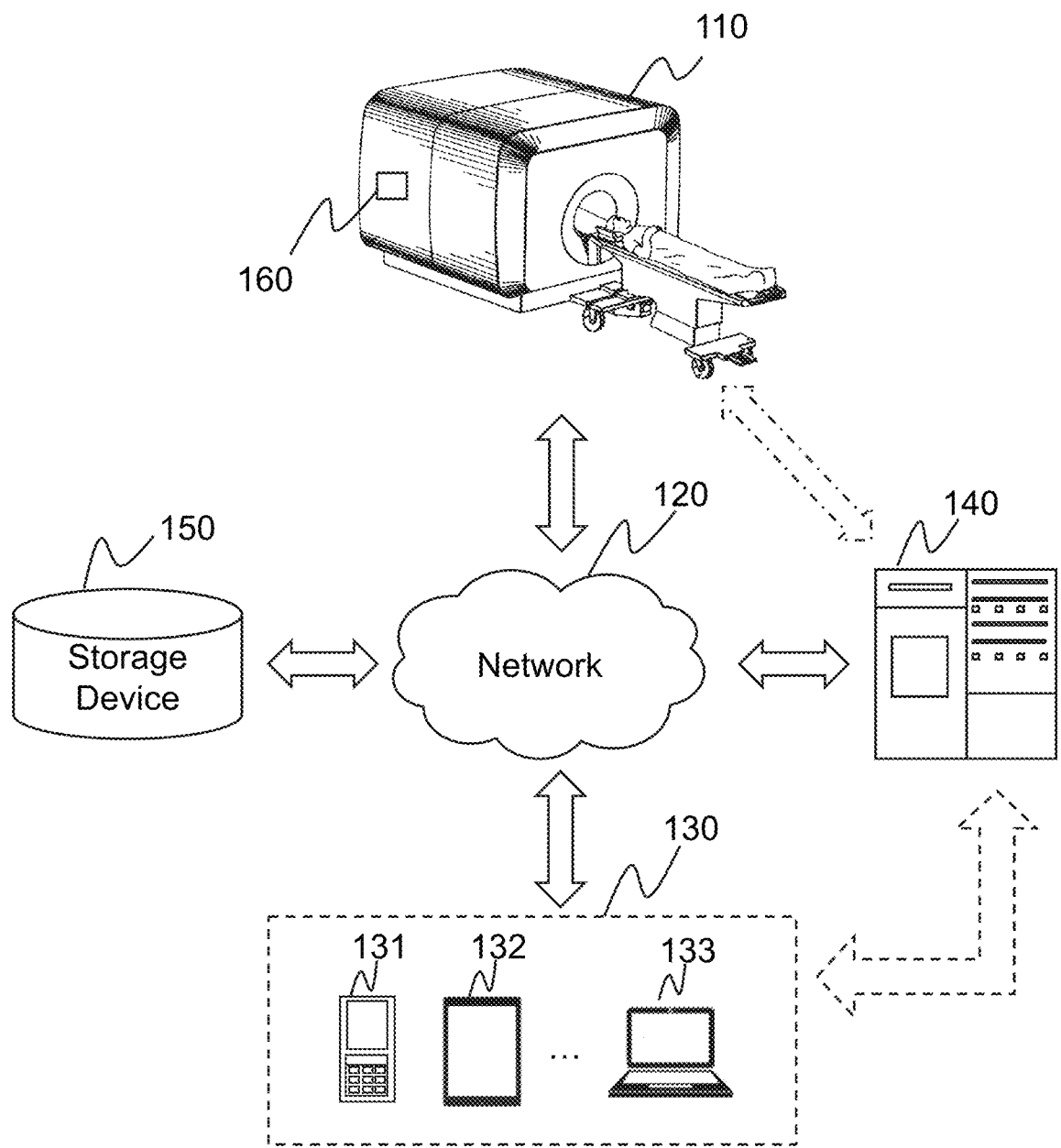
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms ("a", "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second," and "third," etc., are used to distinguish similar objects and do not represent a specific order of the objects.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a noise reduction device. The noise reduction device may include a noise receiving component, a noise reduction component, a processing component, and a housing. The noise receiving component may be configured to receive acoustic noise information of a scanning environment where a medical device is located. The processing component may be configured to control the noise reduction component to generate sound information matching the acoustic noise information received by the noise receiving component. The housing may be configured to support the noise receiving component and the noise reduction component. The sound information may counteract the acoustic noise information, thereby realizing the noise reduction. In addition, the noise reduction component may include at least two noise reduction units, the performance of the noise reduction requirement can be improved and the noise reduction requirement can be satisfied.

Another aspect of the present disclosure relates to a medical device. The medical device may include a noise reduction device. By disposing the noise reduction device on the medical device, the noise reduction may be performed without reducing the performance of the medical device, which can reduce or eliminate the effect of the noise on the performance of the medical device.

FIG. 1 is a schematic diagram illustrating an exemplary medical system according to some embodiments of the present disclosure. As shown in FIG. 1, the medical system 100 may include a medical device 110, a network 120, a terminal device 130, a processing device 140, a storage device 150, and a noise reduction device 160. In some embodiments, the medical device 110, the terminal device 130, the processing device 140, the storage device 150, and/or the noise reduction device 160 may be connected to and/or communicate with each other via a wireless connection, a wired connection, or a combination thereof. The connection among the components of the medical system 100 may be variable. Merely by way of example, the medical device 110 may be connected to the processing device 140 through the network 120, as illustrated in FIG. 1. As another example, the medical device 110 may be connected to the processing device 140 directly. As a further example, the storage device 150 may be connected to the processing device 140 through the network 120, as illustrated in FIG. 1, or connected to the processing device 140 directly.

The medical device 110 may be used for a medical purpose. For example, the medical device 110 may be configured to diagnose, treat, and/or monitor a subject. In some embodiments, the medical device 110 may include an imaging device, a treatment device, a life support device, a medical monitor, etc.

The imaging device may be configured to obtain medical image data (e.g., a scanned image) of the subject. In some embodiments, the imaging device may include a single modality imaging device. For example, the imaging device may include a computed tomography (CT) device, a magnetic resonance imaging (MRI) device, a positron emission tomography (PET) device, an X-ray imaging device, a single-photon emission computed tomography (SPECT) device, an ultrasound device, etc. In some embodiments, the imaging device may include a multi-modality imaging device. Exemplary multi-modality imaging devices may include a positron emission tomography-computed tomography (PET-CT) device, a positron emission tomography-magnetic resonance imaging (PET-MRI) device, a computed tomography-magnetic resonance imaging (CT-MRI) device, etc.

The treatment device may be configured to perform a treatment on the subject. Exemplary treatment devices may include a radiation delivery device (e.g., a radiotherapy (RT) device), an infusion pump, a medical aspirator (e.g., an electric negative pressure aspirator), an electrosurgery, an electrocoagulation, etc. In some embodiments, the RT device may include a conformal radiation therapy device, an image guided radiation therapy (IGRT) device, an intensity modulated radiation therapy (IMRT) device, an intensity modulated arc therapy (IMAT) device, etc.

The life support device may be configured to maintain a bodily function of the subject. Exemplary life support devices may include a medical ventilator, an incubator, an anesthesia machine (e.g., an anesthesia ventilator, an anesthesia sewage system), a heart-lung machine, an extracorporeal membrane oxygenation (ECMO), a dialysis machine, etc.

The medical monitor may be configured to measure vital signs of the subject. Exemplary medical monitors may include an electrocardiogram (ECG) device, an electroencephalogram (EEG) device, a blood pressure device, etc.

Merely by way of example, the medical device 110 may be the MRI device. The MRI device may be configured to scan the subject (or a part of the subject) to acquire scan data, such as MR signals associated with the subject. For example, the MRI device may detect a plurality of MR signals by applying an MR sequence on the subject. In some embodiments, the MRI device may include, for example, a magnetic body, a gradient coil assembly, a radiofrequency (RF) coil assembly, etc. In some embodiments, the MRI device may be a permanent magnet MR scanner, a superconducting electromagnet MR scanner, a resistive electromagnet MR scanner, etc., according to types of the magnetic body. In some embodiments, the MRI device may be a high-field MR scanner, a mid-field MR scanner, a low-field MR scanner, etc., according to the intensity of the magnetic field.

The magnetic body may generate a first magnetic field (also referred to as a main magnetic field) for polarizing the subject to be scanned. The gradient coil assembly may generate a second magnetic field (also referred to as a gradient magnetic field). The gradient coil assembly may include X-gradient coils, Y-gradient coils, and Z-gradient coils. The gradient coil assembly may generate one or more magnetic field gradient pulses to the main magnetic field in the X direction (Gx), the Y direction (Gy), and the Z direction (Gz) to encode the spatial information of the subject. The RF coil assembly may include a plurality of RF coils. The RF coils may include one or more RF transmit coils and/or one or more RF receiver coils. The RF transmit coil(s) may transmit RF pulses to the subject. Under the coordinated action of the main magnetic field, the gradient magnetic field, and the RF pulses, one or more MR signals relating to the subject may be generated according to a pulse sequence. The RF receiver coils may acquire MR signals from the subject according to the pulse sequence. The MR signals may be processed using a transform operation (e.g., Fourier Transform) to fill a k-space to obtain k-space data. The k-space data may be reconstructed according to an MR reconstruction algorithm (e.g., a back projection technique, an iteration reconstruction technique) to obtain an MR image of the subject.

In some embodiments, the subject may include a body, a substance, or the like, or any combination thereof. In some embodiments, the subject may include a specific portion of a body, such as the head, the thorax, an abdomen, or the like, or any combination thereof. In some embodiments, the subject may include a specific organ, such as an esophagus, a trachea, a bronchus, a stomach, a gallbladder, a small intestine, a colon, a bladder, a ureter, a uterus, a fallopian tube, etc. In some embodiments, the subject may include a physical model (e.g., a water phantom). In the present disclosure, "object" and "subject" are used interchangeably.

The network 120 may include any suitable network that can facilitate the exchange of information and/or data for the medical system 100. In some embodiments, one or more components (e.g., the medical device 110, the terminal device 130, the processing device 140, the storage device 150, the noise reduction device 160) of the medical system 100 may communicate information and/or data with one or more other components of the medical system 100 via the network 120. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal device 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal device 130 may be part of the processing device 140.

The processing device 140 may process data and/or information obtained from one or more components (e.g., the medical device 110, the terminal 130, the storage device 150, and/or the noise reduction device 160) of the medical system 100. For example, the processing device 140 may obtain acoustic noise information of a scanning environment where the medical device 110 is located. As another example, the processing device 140 may control the noise reduction device 160 to generate sound information matching the obtained acoustic noise information.

In some embodiments, the processing device 140 may be in communication with a computer-readable storage medium (e.g., the storage device 150) and may execute instructions stored in the computer-readable storage medium.

In some embodiments, the processing device 140 may be a single server or a server group. The server group may be centralized or distributed. In some embodiments, the processing device 140 may be local or remote. For example, the processing device 140 may access information and/or data stored in the medical device 110, the terminal device 130, the storage device 150, and/or the noise reduction device 160 via the network 120. As another example, the processing device 140 may be directly connected to the medical device 110, the terminal device 130, the storage device 150, and/or the noise reduction device 160 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the processing device 140 may be implemented by a computing device. For example, the computing device may include a processor, a storage, an input/output (I/O), and a communication port. The processor may execute computer instructions (e.g., program codes) and perform functions of the processing device 140 in accordance with the techniques described herein. The computer instructions may include, for example, routines, programs, objects, components, data structures, procedures, modules, and functions, which perform particular functions described herein. In some embodiments, the processing device 140, or a portion of the processing device 140 may be implemented by a portion of the terminal device 130.

In some embodiments, the processing device 140 may include multiple processing devices. Thus operations and/or method steps that are performed by one processing device as described in the present disclosure may also be jointly or separately performed by the multiple processing devices. For example, if in the present disclosure, the medical system 100 executes both operation A and operation B, it should be understood that operation A and operation B may also be performed by two or more different processing devices jointly or separately (e.g., a first processing device executes operation A and a second processing device executes operation B, or the first and second processing devices jointly execute operations A and B).

The storage device 150 may store data/information obtained from the medical device 110, the terminal device 130, the processing device 140, the noise reduction device 160, and/or any other component of the medical system 100. In some embodiments, the storage device 150 may include a mass storage, a removable storage, a volatile read-and-write memory, a read-only memory (ROM), or the like, or any combination thereof. In some embodiments, the storage device 150 may store one or more programs and/or instructions to perform exemplary methods described in the present disclosure.

In some embodiments, the storage device 150 may be connected to the network 120 to communicate with one or more other components (e.g., e.g., the medical device 110, the terminal device 130, the processing device 140, the noise reduction device 160) of the medical system 100. One or more components of the medical system 100 may access the data or instructions stored in the storage device 150 via the network 120. In some embodiments, the storage device 150 may be directly connected to or communicate with one or more other components of the medical system 100. In some embodiments, the storage device 150 may be part of the processing device 140.

The noise reduction device 160 may be configured to reduce or eliminate acoustic noise of a scanning environment where the medical device 110 is located. For example, when an MRI device scans a subject (e.g., a patient), a gradient field formed by a gradient coil assembly of the MRI device changes rapidly with time. According to the law of electromagnetic induction, an alteration of a current leads to an alteration of a magnetic field. Accordingly, when the gradient field needs to be changed, the current in the gradient coil assembly may be changed. In addition, wires carrying the current are subjected to the Lorentz force. Accordingly, when the gradient field needs to be switched, the current changes drastically and the Lorentz force changes accordingly. The Lorentz force may cause mechanical vibrations and displacements of the gradient coil assembly, resulting in that the gradient coil assembly may hit components (e.g., a gantry, a housing) of the MRI device, thereby resulting in noise. The noise is transmitted to a scanning chamber where the patient is located through air or mechanical vibrations of components of the MRI device, which in turn reduces the comfort of the patient during the scan. Accordingly, the noise reduction device 160 is used to reduce or eliminate the acoustic noise. For example, the noise reduction device 160 may receive acoustic noise information of a scanning environment where the medical device 110 is located, and generate sound information matching the received acoustic noise information.

In some embodiments, the noise reduction device 160 may be disposed on various suitable positions for reducing or eliminating the acoustic noise. For example, the noise reduction device 160 may be arranged on a component (e.g., the RF coils, a cavity around an examination space, a scanning table, a housing) of the medical device 110. In some embodiments, the noise reduction device 160 may be disposed on a suitable position outside the medical device 110, for example, on the outer surface of a scan cavity, on the ceiling of a treatment room, on the floor of the treatment room, on a holder outside the medical device 110, etc. In some embodiments, the noise reduction device 160 may be part of the medical device 110. More descriptions of the noise reduction device 160 may be found elsewhere in the present disclosure (e.g., FIGS. 2 and 6A-10, and the descriptions thereof).

It should be noted that the above description regarding the medical system 100 is merely provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical system 100 may include one or more additional components, and/or one or more components of the medical system 100 described above may be omitted. In some embodiments, a component of the medical system 100 may be implemented on two or more sub-components. Two or more components of the medical system 100 may be integrated into a single component.

Figure 2:
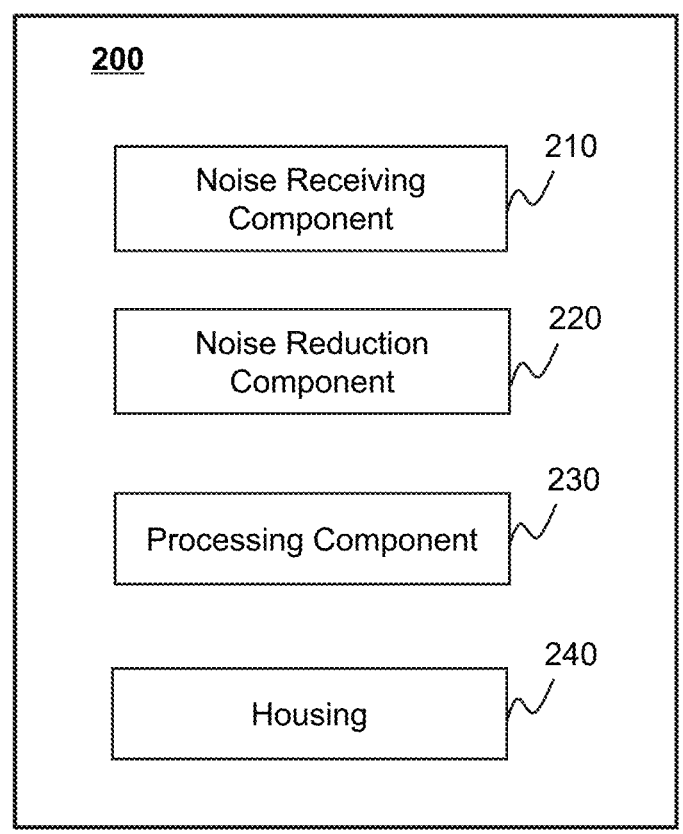
FIG. 2 is a block diagram illustrating an exemplary noise reduction device according to some embodiments of the present disclosure.

FIG. 2 is a block diagram illustrating an exemplary noise reduction device according to some embodiments of the present disclosure. A noise reduction device 200 may be an embodiment of the noise reduction device 160 described in FIG. 1.

As shown in FIG. 2, the noise reduction device 200 may include a noise receiving component 210, a noise reduction component 220, a processing component 230, and a housing 240.

The noise receiving component 210 may be configured to receive acoustic noise information of a scanning environment where a medical device (e.g., the medical device 110) is located. For example, the noise receiving component 210 may include a microphone. In some embodiments, the acoustic noise information may include parameter(s) (e.g., a frequency, an amplitude, a timber, a phase) of acoustic noise corresponding to the scanning environment. In some embodiments, the noise receiving component 210 may be located on an inner surface or an outer surface of the housing 240. More descriptions of the noise receiving component 210 may be found elsewhere in the present disclosure (e.g., FIGS. 6A-10 and the descriptions thereof).

The noise reduction component 220 may be configured to generate sound information matching the acoustic noise information received by the noise receiving component 210. The sound information may include parameter(s) (e.g., a frequency, an amplitude, a timber, a phase) of an anti-sound corresponding to the acoustic noise information. For example, the amplitude of the anti-sound may be the same as or substantially the same as the amplitude of the acoustic noise information; the phase of the anti-sound may be opposite to or substantially opposite to the phase of the acoustic noise information. In some embodiments, the sound information may counteract the acoustic noise information, thereby realizing the noise reduction. In some embodiments, the noise reduction component 220 may be located on the outer surface of the housing 240. In some embodiments, a type of the noise reduction component 220 may be selected with respect to a type of the medical device. For example, the noise reduction is designed for an MRI device, the noise reduction component 220 may include a ceramic piezoelectric speaker which does not produce electromagnetic interference and/or radiation. As another example, to match acoustic noise information, the noise reduction component 220 may include a plurality of ceramic piezoelectric speakers (e.g., two ceramic piezoelectric speakers) with different shapes and/or thicknesses.

In some embodiments, the noise reduction component 220 may include a speaker. In some embodiments, the noise reduction component 220 may include a flat panel speaker and/or a curved speaker. The flat panel speaker may have advantages including, for example, light weight, easy installation, high security, high efficiency of electroacoustic conversion, etc. The curved speaker may match with a curvature of the housing 240, which can improve the integrality of the noise reduction device 200, optimize the sound transmission, and improve the performance of the noise reduction.

In some embodiments, a parameter (e.g., a shape, a length, a width, a radius, and/or a thickness) of the noise reduction component 220 may be designed according to noise reduction requirement.

In some embodiments, the noise reduction component 220 may include at least two noise reduction units. The at least two noise reduction units may be disposed on two opposite sides of the housing 240. In some embodiments, parameters (e.g., a shape, a length, a width, a radius, and/or a thickness) of the at least two noise reduction units may be at least partially different.

More descriptions of the noise reduction component 220 may be found elsewhere in the present disclosure (e.g., FIGS. 6A-10 and the descriptions thereof).

The processing component 230 may be configured to control the noise reduction component 220 to generate the sound information matching the acoustic noise information received by the noise receiving component 210. For example, the processing component 230 may obtain the acoustic noise information received by the noise receiving component 210, determine sound information matching the noise information, and control the noise reduction component 220 to generate the sound information. More descriptions regarding the generation of the sound information may be found elsewhere in the present disclosure (e.g., FIG. 12 and the descriptions thereof). In some embodiments, the processing component 230 may be similar to the processing device 140 as described in connection with FIG. 1.

In some embodiments, the processing component 230 may include a signal processor (not shown). The signal processor may be configured to determine the sound information matching the received acoustic noise information. In some embodiments, the signal processor may include an input terminal and an output terminal. The input terminal of the signal processor may be connected to an output terminal of the noise receiving component 210, and the output terminal of the signal processor may be connected to an input terminal of the noise reduction component 220. Accordingly, the signal processor may obtain a first signal including the acoustic noise information from the noise receiving component 210, and transmit a second signal including the sound information to the noise reduction component 220. The noise reduction component 220 may generate the sound information based on the second signal including the sound information. In some embodiments, the signal processor may determine the second signal based on the first signal by using a signal processing model. The signal processing model may indicate a corresponding relationship (e.g., a function) between the first signal and the second signal. More descriptions of the signal processing model may be found elsewhere in the present disclosure (e.g., FIG. 3 and the descriptions thereof).

The housing (also referred to as "first housing") 240 may be configured to support the noise receiving component 210 and the noise reduction component 220. In some embodiments, at least one through hole may be disposed at a position of the housing 240 where the noise reduction component 220 is located. For example, the at least one through hole may include a plurality of through holes, and the plurality of through holes may be disposed in rows and columns. In some embodiments, a size of the at least one through hole may be within a preset range. The preset range may be determined based on a system default setting or set manually by a user (e.g., a technician, a physicist). More descriptions of the housing 240 may be found elsewhere in the present disclosure (e.g., FIGS. 6A-10, and the descriptions thereof).

In some embodiments, the noise reduction device 200 may also include a support component (not shown). The support component may be configured to support the noise reduction component 220. In some embodiments, the support component may include a support frame and a vibration isolation structure. The vibration isolation structure may be located in the support frame or located between the support frame and the noise reduction component 220. In some embodiments, the support frame may include a frame body and a side edge. The side edge may be disposed on the frame body and protrudes from the frame body. In some embodiments, the support frame may further include a plate structure. The plate structure may be fixedly connected to the side edge. More descriptions of the support component may be found elsewhere in the present disclosure (e.g., FIGS. 6A-10, and the descriptions thereof).

In some embodiments, the noise reduction device 200 may further include a second housing (not shown) located outside the housing 240. The second housing and the housing 240 may form an enclosed structure. For example, the second housing and the housing 240 may form an accommodation chamber, and the noise reduction component 220 may be located on the housing 240 and/or the second housing. More descriptions of the second housing may be found elsewhere in the present disclosure (e.g., FIGS. 6A-10, and the descriptions thereof).

In some embodiments, the noise reduction device 200 may include two or more noise receiving components and/or two or more noise reduction components. For example, the noise reduction device 200 may include a first noise receiving component located on an inner side wall of a chamber, a first noise reduction component located on an outer surface of the housing 240, a second noise receiving component located on an inner surface of the housing 240, and a second noise reduction component located on the inner surface of the housing 240. The processing component 230 may be configured to control the first noise reduction component to generate first sound information matching first acoustic noise information received by the first noise receiving component and/or control the second noise reduction component to generate second sound information matching second acoustic noise information received by the second noise receiving component. The first acoustic noise information and the second acoustic noise information may be from a scanning environment where a medical device (e.g., the medical device 110) is located. In some embodiments, a count of the noise receiving component(s) and/or a count of the noise reduction component(s) may be set or adjusted according to noise reduction requirement, which are not intended to be limiting.

It should be noted that the noise reduction device 200 is provided for illustration purposes, and is not intended to limit the scope of the present disclosure. For persons having ordinary skills in the art, multiple variations and modifications may be made under the teachings of the present disclosure. However, those variations and modifications do not depart from the scope of the present disclosure. For example, the noise reduction device 200 may further include a noise-absorbing structure (e.g., noise-absorbing cotton) on the housing 240 or other positions of the noise reduction device 200 to initially reduce the acoustic noise information.

Figure 3:
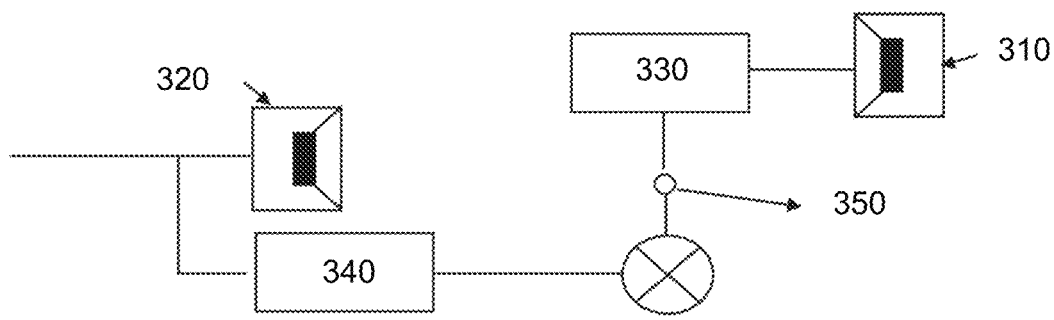
FIG. 3 is a schematic diagram illustrating an exemplary signal processing model according to some embodiments of the present disclosure.

FIG. 3 is a schematic diagram illustrating an exemplary signal processing model according to some embodiments of the present disclosure. A signal processing model 300 may be used to generate a second signal including sound information based on a first signal including acoustic noise information. The signal processing model may indicate a corresponding relationship (e.g., a function) between the first signal and the second signal.

As illustrated in FIG. 3, the signal processing model 300 may include a primary sound source 310, a secondary sound source 320, a primary transfer impedance 330 for the primary sound source 310, a secondary transfer impedance 340 for the secondary sound source 320, and an error sound generator 330. The primary sound source 310 may correspond to the first signal including the acoustic noise information. The secondary sound source 320 may correspond to the second signal including the sound information.

In some embodiments, a sound pressure signal e of the error sound generator 330 may be determined according to Equation (1):

$$e = Z_a \times Q_a + Z_s \times Q_s, \qquad (1)$$

where $Q_a$ represents a sound pressure of the primary sound source 310, $Z_a$ represents the primary transfer impedance 330 for the primary sound source 310, $Q_s$ represents a sound pressure of the secondary sound source 320, and $Z_s$ represents the secondary transfer impedance 340 for the secondary sound source 320.

In order to realize the noise reduction function, a value of a sound energy at the error sound generator 330 should be minimized. Merely by way of example, a performance function j may be defined as an acoustic potential energy (to simply the problem, only the acoustic potential energy is considered and the effect of the kinetic energy of the sound field is ignored) at the error sound generator 330 according to Equation (2):

$$J = e^* e = Q_s^* \times A \times Q_s + Q_s^* \times b + b^* \times Q_s + c, \qquad (2)$$

where * represents a conjugate transpose operation, × represents product operation, $A = Z_s^* \times Z_s$, $b = Z_s^* \times Z_a \times Q_a$, and $c = Q_a^* \times Z_a^* \times Z_a \times Q_a$.

Further, a vector of an optimized value of $Q_s$ may be obtained by taking the derivative of the performance function J with respect to the secondary sound source $Q_s$ and setting the result to 0 according to Equation (3):

$$Q_s = = -A^{-1}b = -(Z_s^* \times Z_s)^{-1} \times (Z_s^* \times Z_a \times Q_a). \qquad (3)$$

Accordingly, the value $Q_s$ of the secondary sound source 320 may be adjusted to be equal to the optimized value of $Q_s$.

In some embodiments, a minimum residual amount $J_{min}$ of the acoustic potential energy at the error sound generator 330 may be determined according to Equation (4):

$$J_{min} = c + b^* \times Q_s. \qquad (4)$$

Thus, a noise reduction ratio R of the signal processing model 300 may be obtained according to Equation (5):

$$R = (c - J_{min})/c = -(b^* \times Q_s)/c. \qquad (5)$$

It also can be seen that the value $Q_s$ of the secondary sound source 320 may directly affect the noise reduction ratio R of the signal processing model 300.

Figure 4A:
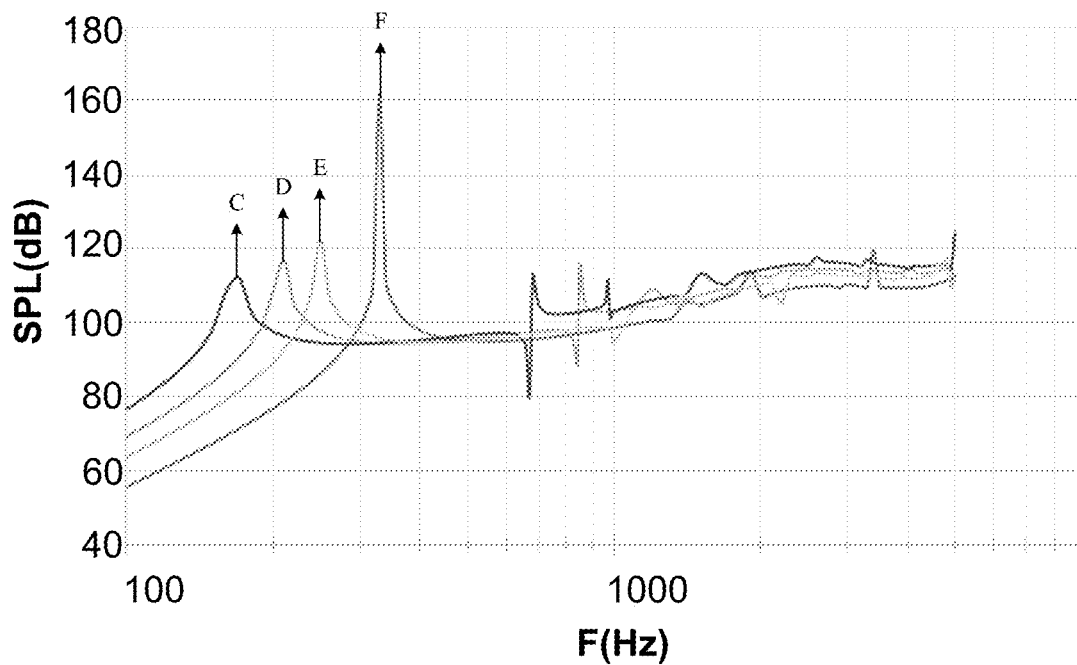
FIG. 4A and FIG. 4B are schematic diagrams illustrating exemplary simulation results corresponding to different thicknesses or different shapes of flat panel speakers according to some embodiments of the present disclosure.
Figure 4B:
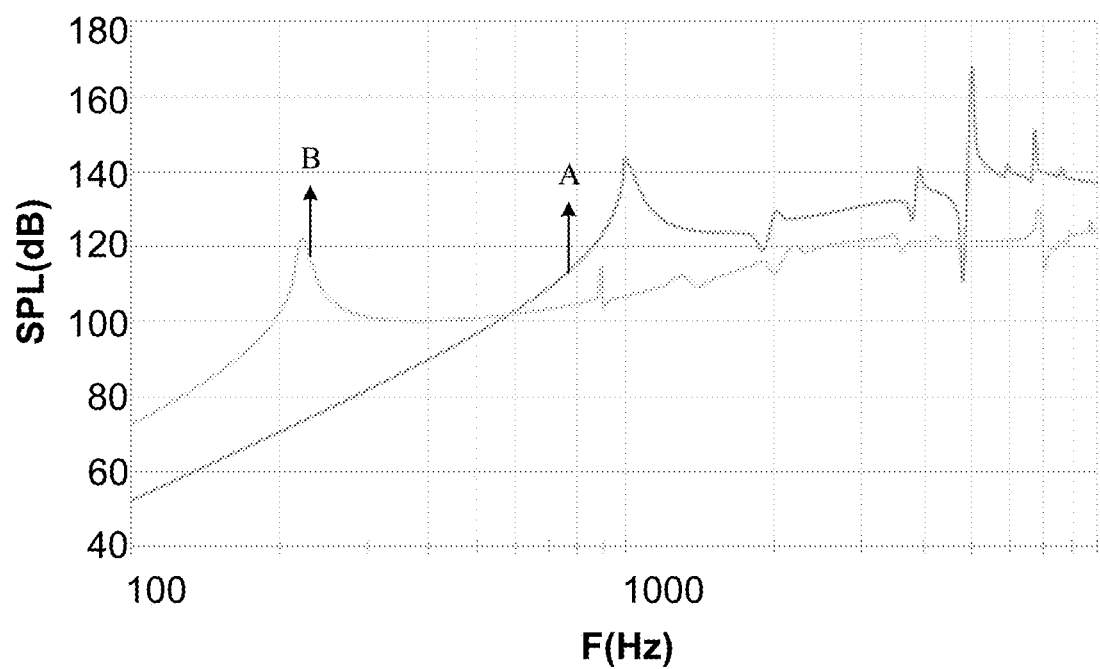

FIG. 4A and FIG. 4B are schematic diagrams illustrating exemplary simulation results corresponding to different thicknesses or different shapes of flat panel speakers according to some embodiments of the present disclosure.

In some embodiments, as described in connection with FIG. 2, a parameter of the noise reduction component may be designed according to noise reduction requirement. Exemplary parameters may include a shape, a length, a width, a radius, a thickness, or the like, or any combination thereof.

In some embodiments, a thickness of a noise reduction component may be designed according to noise reduction requirement. Specifically, for a noise reduction component including a flat panel speaker, a radiated sound field of the noise reduction component may be a superposition of a series of radiated sounds generated under a bending vibration mode, and a frequency spectrum distribution of a mid-low frequency sound radiation of the flat panel speaker may be affected by the vibration mode (e.g., the bending vibration mode with a high radiation efficiency) of the flat panel speaker. Accordingly, by disposing the flat panel speakers with different thicknesses, the superposition of radiated sounds generated under the vibration mode may be improved, thereby satisfying the noise reduction requirement.

For example, as illustrated in FIG. 4A, curves "C," "D," "E," and "F" are radiation simulation results corresponding to four flat panel speakers (e.g., ceramic piezoelectric flat panel speakers) with different thicknesses. For example, a length of each of the four flat panel speakers may be 100 millimeters, and a width of each of the four flat panel speakers may be 80 millimeters. A thickness of a flat panel speaker corresponding to the curve "C" may be 0.8 millimeters, a thickness of a flat panel speaker corresponding to the curve "D" may be 1 millimeter, a thickness of a flat panel speaker corresponding to the curve "E" may be 1.2 millimeters, and a thickness of a flat panel speaker corresponding to the curve "F" may be 1.6 millimeters. It can be seen that different thicknesses may correspond to different sound radiation performances in the low-to-mid frequency range. Accordingly, a combination of flat panel speakers with different thicknesses can improve the sound radiation performance in the entire low-to-mid frequency range.

In some embodiments, a shape of the noise reduction component may be designed according to noise reduction requirement. For example, as illustrated in FIG. 4B, curves "A" and "B" are radiation simulation results corresponding to two flat panel speakers (e.g., ceramic piezoelectric flat panel speakers) with different shapes. For example, a length, a width, and a thickness of a first flat panel speaker corresponding to the curve "A" may be 40 millimeters, 76 millimeters, and 0.8 millimeters, respectively; a length, a width, and a thickness of a second flat panel speaker corresponding to the curve "B" may be 68 millimeters, 88 millimeters, and 0.8 millimeters, respectively. It can be seen that in a low frequency band, a sound pressure level of the second flat panel speaker may be higher than a sound pressure level of the first flat panel speaker; in a high frequency band, the sound pressure level of the first flat panel speaker may be higher than the sound pressure level of the second flat panel speaker. Accordingly, in the low frequency band, the second flat panel speaker may be selected to improve the performance of the noise reduction; in the high frequency band, the first flat panel speaker may be selected to improve the performance of the noise reduction.

Figure 5A:
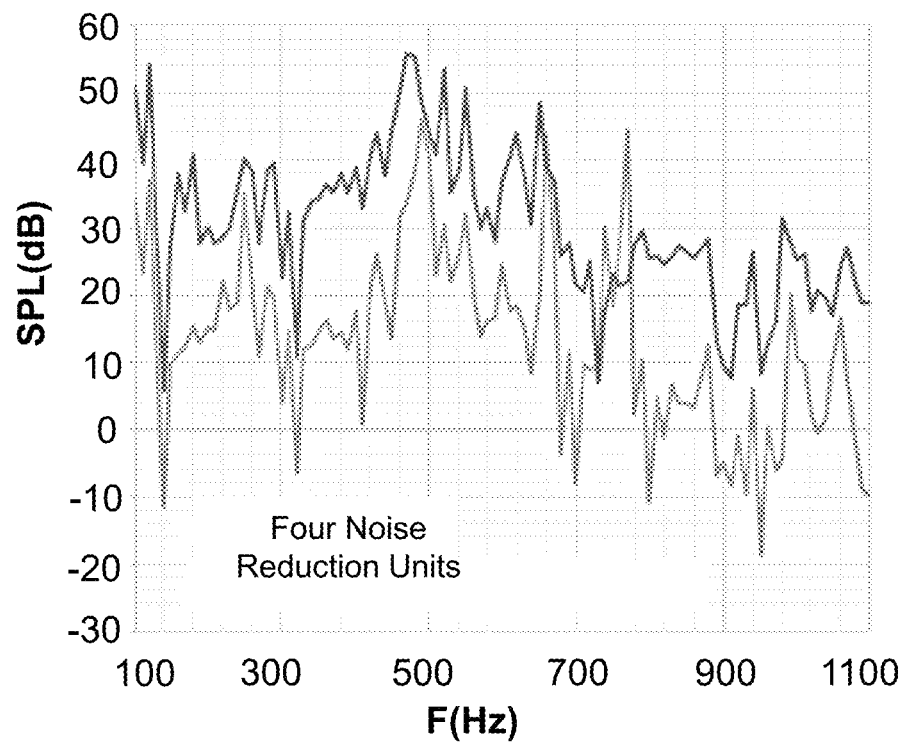
FIG. 5A and FIG. 5B are schematic diagrams illustrating simulation results of a noise reduction component including multiple noise reduction units according to some embodiments of the present disclosure.
Figure 5B:
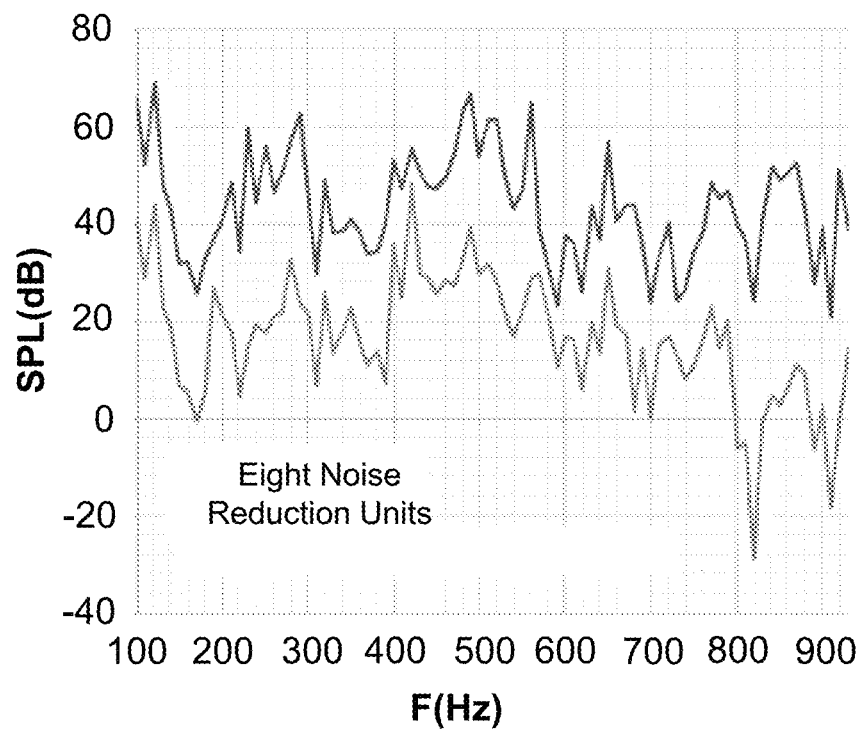

FIG. 5A and FIG. 5B are schematic diagrams illustrating simulation results of a noise reduction component including multiple noise reduction units according to some embodiments of the present disclosure.

In some embodiments, as described in connection with FIG. 2, the noise reduction component may include at least two noise reduction units. For example, the noise reduction component includes four noise reduction units (e.g., ceramic piezoelectric flat panel speakers) symmetrically disposed on two opposite sides of a first housing. As illustrated in FIG. 5A, the effect of the noise reduction corresponding to the four noise reduction units is higher than that of only one noise reduction unit. As another example, the noise reduction component includes eight noise reduction units (e.g., ceramic piezoelectric flat panel speakers) symmetrically disposed on two opposite sides of a second housing. As illustrated in FIG. 5B, the effect of the noise reduction corresponding to the eight noise reduction units is higher than that of only one noise reduction unit.

It should be noted that the installation position(s) and/or the count of the noise reduction units are not intended to be limiting. By disposing the at least two noise reduction units, the performance of the noise reduction requirement can be improved and the noise reduction requirement can be satisfied.

In some embodiments, parameters (e.g., a shape, a length, a width, a radius, a thickness) of the at least two noise reduction units may be at least partially different. Accordingly, the at least two noise reduction units can satisfy different noise reduction requirements, thereby improving the performance of the noise reduction.

FIGS. 6A-6D are schematic diagrams illustrating an exemplary noise reduction device according to some embodiments of the present disclosure. The noise reduction device 600 may be an embodiment of the noise reduction device 160 described in FIG. 1.

In some embodiments, the noise reduction device 600 may be disposed on a medical device (e.g., the medical device 110). For illustration purposes, the medical device may be an MRI device including a head coil assembly.

Figure 6A:
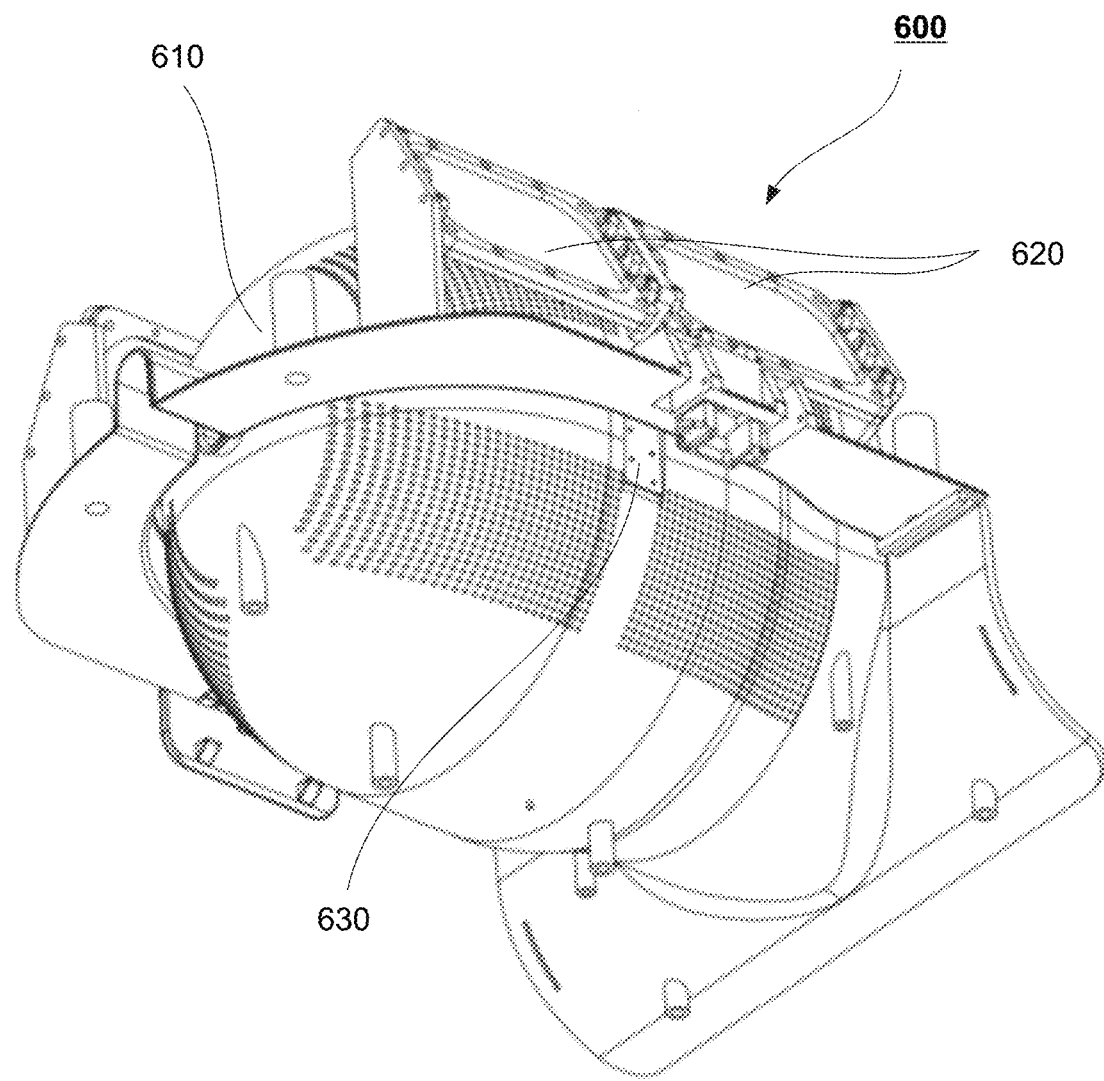
FIGS. 6A-6D are schematic diagrams illustrating an exemplary noise reduction device according to some embodiments of the present disclosure.

As shown in FIG. 6A, the noise reduction device 600 may include a housing 610, a noise reduction component 620, and a noise receiving component 630.

Figure 6B:
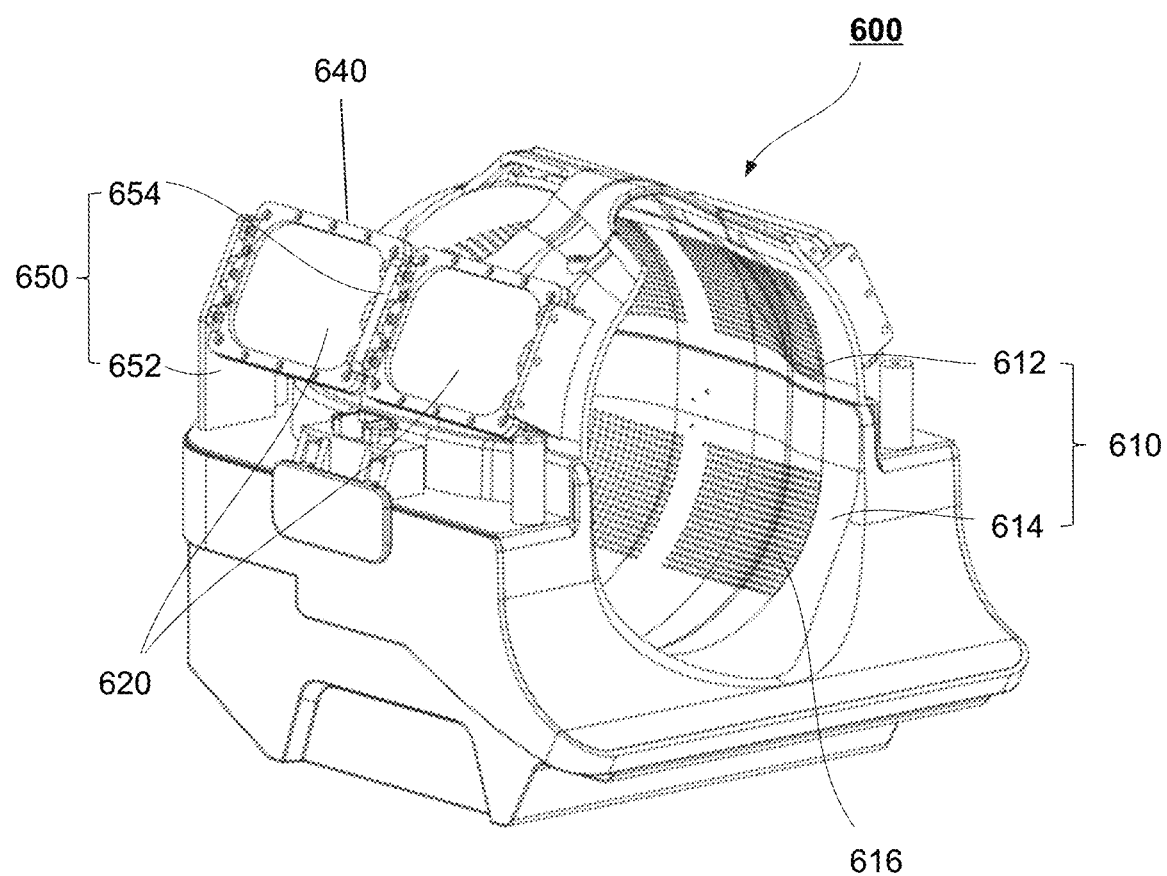

The housing 610 may be configured to support and protect components of the noise reduction device 600 and/or components of the MRI device. In some embodiments, the housing 610 may be a portion of the MRI device. For example, the housing 610 may be an inner housing of an MRI device. In some embodiments, as illustrated in FIG. 6B, the housing 610 may be a hollow structure forming an accommodation chamber where a subject to be scanned can be located. In some embodiments, as illustrated in FIG. 6B, the housing 610 may include a first sub-housing 612 and a second sub-housing 614. The first sub-housing 612 may be disposed above the second sub-housing 614.

The noise reduction component 620 may be used for the noise reduction. In some embodiments, the noise reduction component 620 may generate sound information matching acoustic noise information received by the noise receiving component 630. For example, an amplitude of the sound information may be the same as or substantially the same as an amplitude of the acoustic noise information, and a phase of the sound information may be opposite to or substantially opposite to a phase of the acoustic noise information. In some embodiments, the noise reduction component 620 may include a flat panel speaker or a curved speaker. For example, the noise reduction component 620 may be made of a ceramic piezoelectric sheet, and the ceramic piezoelectric sheet may be configured as a flat sounding membrane.

Figure 6C:
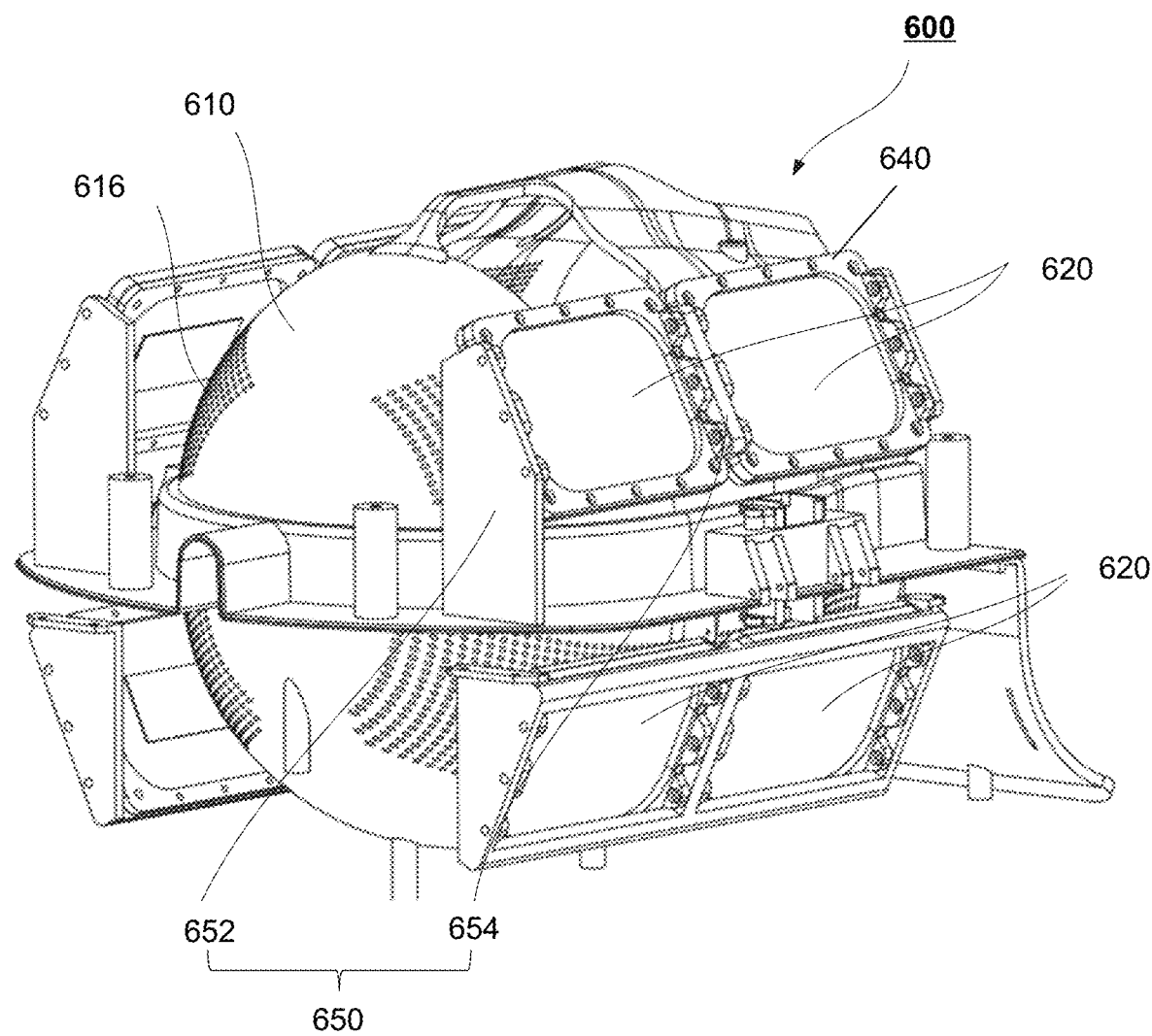

In some embodiments, as illustrated in FIG. 6B, the noise reduction component 620 may be disposed on an outer surface of the housing 610. In some embodiments, the noise reduction component 620 may include at least two noise reduction units (e.g., 626 illustrated in FIG. 7). In some embodiments, the at least two noise reduction units may be disposed on sides of the housing 610. For example, as illustrated in FIG. 6B and FIG. 6C, the at least two noise reduction units may be disposed on two opposite sides of the housing 610, respectively. In some embodiments, the at least two noise reduction units may be symmetrically disposed on the two opposite sides of the housing 610.

In some embodiments, the at least two noise reduction units disposed on the two opposite sides of the housing 610 may cooperate with each other to reduce the acoustic noise information. Merely by way of example, the at least two noise reduction units may correspond to the left ear and the right ear of the subject, and generate corresponding sound information for the noise reduction on the two opposite sides of the subject, respectively. Accordingly, the left ear and the right ear of the subject may be subjected to a same extent of the acoustic noise information, which can improve the comfort of the subject during the scan.

The noise receiving component 630 may be configured to receive the acoustic noise information of the scanning environment where the MRI device is located. In some embodiments, the noise receiving component 630 may include a microphone or other components that can receive the acoustic noise information. In some embodiments, the noise receiving component 630 may be disposed on the housing 610. In some embodiments, the noise receiving component 630 may be disposed on an inner surface or an outer surface of the housing 610.

In some embodiments, the noise receiving component 630 and/or the noise reduction component 620 may be electrically connected to a processing component (e.g., the processing device 140, the processing component 230). For example, an input terminal of the processing component may be electrically connected to an output terminal of the noise receiving component 630, and an output terminal of the processing component may be electrically connected to an input terminal of the noise reduction component 620.

In some embodiments, during the noise reduction, the noise receiving component 630 (e.g., located on an outer surface of the housing 610) may receive acoustic noise of the scanning environment where the MRI device is located and transmit the acoustic noise to the processing component. The processing component may process the acoustic noise to obtain the acoustic noise information (e.g., an amplitude of the acoustic noise). Further, the processing component may determine the sound information based on the acoustic noise information and transmit the sound information to the noise reduction component 620. The noise reduction component 620 may generate corresponding sound (e.g., a sound signal) based on the sound information for the noise reduction. The sound may counteract the acoustic noise, thereby realizing the noise reduction. Accordingly, the noise heard by the subject can be reduced and the comfort of the subject during the scan can be improved.

According to some embodiments of the present disclosure, the sound information generated by the noise reduction component 620 may counteract the acoustic noise information, which can reduce the noise heard by the subject, thereby improving the comfort and experience of the subject during the scan.

In some embodiments, at least one through hole 616 may be disposed at a position of the housing 610 where the noise reduction component 620 is located. In some embodiments, a shape of the at least one through hole 616 may include a circle, a square, an ellipse, an triangle, or the like, or any combination thereof. In some embodiments, the at least one through hole 616 may be disposed in rows and columns. In some embodiments, a size of the at least one through hole 616 may be within a preset range. The preset range may be determined based on a system default setting or set manually by a user. For example, considering a ruggedness of the housing 610, the preset range may be determined in a range of 0 to 2 millimeters.

By disposing the at least one through hole 616, the transmission of the sound information generated by the noise reduction component 620 can be speeded up, which can improve the efficiency of the counteraction between the sound information and the acoustic noise information, thereby improving the efficiency of the noise reduction.

In some embodiments, as illustrated in FIG. 6B and FIG. 6C, the noise reduction device 600 may also include a support component 640. The support component 640 may be configured to support the noise reduction component 620. In some embodiments, the support component 640 may include a frame structure or other structures that can support the noise reduction component 620. More descriptions of the support component 640 may be found elsewhere in the present disclosure (e.g., FIG. 7 and the descriptions thereof).

In some embodiments, as illustrated in FIG. 6B and FIG. 6C, the noise reduction device 600 may also include a fixing structure 650. The fixing structure 650 may be configured to support or fix the support component 640 and/or the noise reduction component 620. In some embodiments, the fixing structure 650 may include a first plate 652 and a second plate 654. More descriptions of the fixing structure 650 may be found elsewhere in the present disclosure (e.g., FIG. 7 and the descriptions thereof).

Figure 6D:
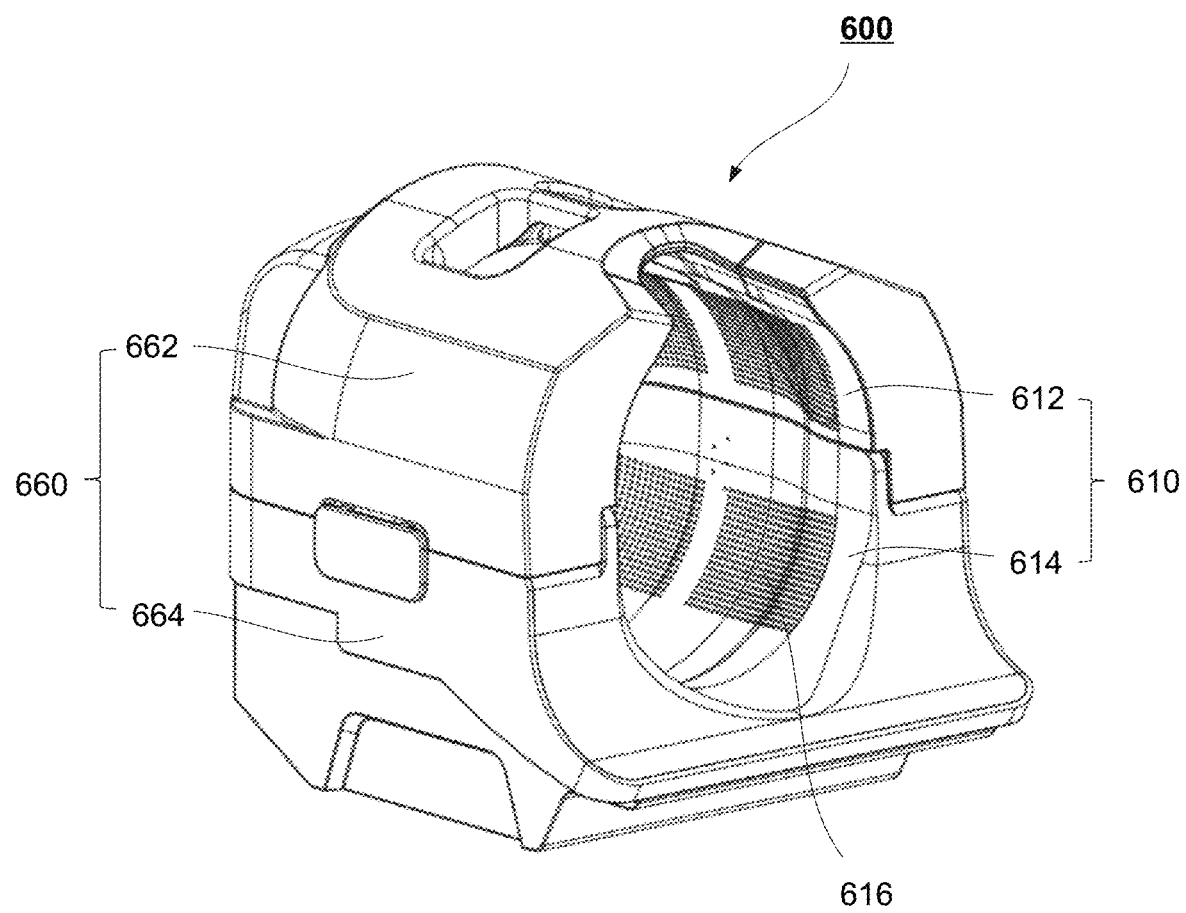

In some embodiments, as illustrated in FIG. 6D, the noise reduction device 600 may include a second housing 660. The second housing 660 may be located outside the housing 610. For example, the second housing 660 may be disposed around an outer side of the housing 610. In some embodiments, an accommodation chamber may be formed between the second housing 660 and the housing 610, and the accommodation chamber may be used to dispose the noise receiving component 630 and/or the noise reduction component 620.

In some embodiments, the second housing 660 may include a third sub-housing 662 and a fourth sub-housing 664. As described in connection with above, the first sub-housing 612 may be disposed above the second sub-housing 614, and the third sub-housing 662 may be disposed above the fourth sub-housing 664. Further, the first sub-housing 612 may be connected to the third sub-housing 662 to form an upper housing, and the second sub-housing 614 may be connected to the fourth sub-housing 664 to form a lower housing. In some embodiments, the upper housing may be detachably connected to the lower housing. In some embodiments, the upper housing and the lower housing may be an integral structure.

In some embodiments, the upper housing may include at least two noise reduction units, and the lower housing may include at least two noise reduction units. The noise reduction units may cooperate with each other to realize the noise reduction. Merely by way of example, the upper housing may include four noise reduction units, and the four noise reduction units may be symmetrically disposed on the two opposite sides of the accommodating chamber of the housing 610. The lower housing may include four noise reduction units, and the four noise reduction units may be symmetrically disposed on the two opposite sides of the accommodating chamber of the housing 610.

In some embodiments, the noise reduction device 600 may further include an end plate (not shown). The end plate may be used to connect the second housing 660 and the housing 610, so that the second housing 660 and the housing 610 may form an enclosed structure or an enclosed space. Accordingly, exposure of components of the noise reduction device 600 and/or components of the MRI device may be avoided, thereby improving the safety of the scan.

According to some embodiments of the present disclosure, by disposing the noise reduction device 600 on the MRI device, the noise reduction device 600 can be integrated on the MRI device, which can simplify the use of the noise reduction device 600 and improve the efficiency of the noise reduction.

It should be noted that the noise reduction device 600 is provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure.

For example, a noise reduction device may be disposed on a head coil assembly. The noise reduction device may include a housing and one or more noise reduction components. The housing may include a first housing and a second housing. The first housing may be disposed above the second housing, and the first housing and the second housing may be formed an accommodation chamber. The one or more noise reduction components may be disposed on the first housing and/or the second housing, and the one or more noise reduction components may be driven to generate sound information matching acoustic noise information of a scanning environment where the head coil assembly is located.

Figure 7:
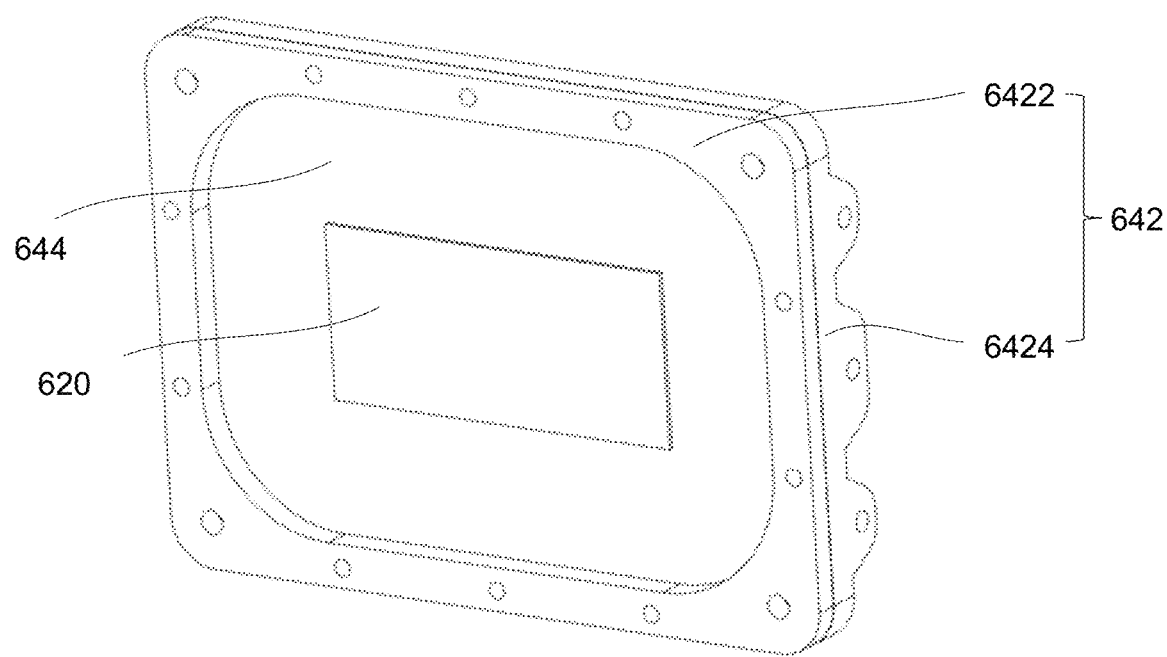
FIG. 7 is a schematic diagram illustrating an exemplary support component according to some embodiments of the present disclosure.

FIG. 7 is a schematic diagram illustrating an exemplary support component used for supporting a noise reduction component according to some embodiments of the present disclosure.

In some embodiments, as illustrated in FIG. 7, the support component 640 may include a support frame 642 and a vibration isolation structure 644.

The support frame 642 may be configured to support the noise reduction component 620 (or a noise reduction unit thereof) and the vibration isolation structure 644, so that the noise reduction component 620 and the vibration isolation structure 644 can be disposed outside the housing 610.

The vibration isolation structure 644 may be used for vibration isolation. In some embodiments, the vibration isolation structure 644 may be disposed in the support frame 642 or located between the support frame 642 and the noise reduction component 620. When the noise reduction component 620 is disposed on the support frame 642 through the vibration isolation structure 644, vibrations on the support frame 642 can be prevented from being directly transmitted to the noise reduction component 620, which can improve the performance of the noise reduction component 620, thereby ensuring the performance of the noise reduction. In some embodiments, the vibration isolation structure 644 may include a vibration isolation pad. The vibrations transmitted by the support frame 642 may be reduced (e.g., buffered) by the vibration isolation structure 644, thereby reducing the vibrations received by the noise reduction component 620 and improving the performance of the noise reduction component 620.

In some embodiments, the noise reduction component 620 (or a noise reduction unit thereof) may be disposed on a middle region of the vibration isolation structure 644. Accordingly, the vibrations of the noise reduction component 620 can be balanced, thereby improving the performance of the noise reduction component 620. In some embodiments, as described in connection with above, the noise reduction component 620 may include at least two noise reduction units. Accordingly, each of the at least two noise reduction units may correspond to a support frame 642 and a vibration isolation structure 644.

In some embodiments, two vibration isolation structures 644 may be disposed on two opposite sides of the support frame 642, and two opposite sides of the noise reduction component 620 may be connected to the two vibration isolation structures 644, respectively. For example, one vibration isolation structure 644 may be disposed on one surface of the support frame 642, and the other one vibration isolation structure 644 may be disposed on the other surface of the support frame 642. Accordingly, a space between the two vibration isolation structures 644 can be used for disposing the noise reduction component 620, wherein one surface of the noise reduction component 620 may be connected to a surface of one vibration isolation structure 644, and another surface of the noise reduction component 620 may be connected to a surface of the other one vibration isolation structure 644.

In some embodiments, as illustrated in FIG. 7, the support frame 642 may include a frame body 6422 and a side edge 6424.

The frame body 6422 may be used to fix the vibration isolation structure 644. In some embodiments, the frame body 6422 may be a hollow structure including a hollow space for accommodating the noise reduction component 620 and/or the vibration isolation structure 644. In some embodiments, edges of the vibration isolation structure 644 may be fixedly connected to the frame body 6422. In some embodiments, the middle region of the vibration isolation structure 644 may correspond to the accommodation space of the frame body 6422 and be a suspended portion. The noise reduction component 620 may be disposed on the suspended portion of the vibration isolation structure 644. In some embodiments, as described in connection with above, the two vibration isolation structure 644 may be disposed on two opposite sides of the frame body 6422.

In some embodiments, the frame body 6422 may include a fixing hole for fixing the vibration isolation structure 644. In some embodiments, the vibration isolation structure 644 may be fixed to the frame body 6422 through a connection, such as a glue connection, a welding connection, a thread connection, or the like, or any combination thereof.

The side edge 6424 may be disposed on the frame body 6422 and protrude from the frame body 6422. In some embodiments, the side edge 6424 may be used to fix the support component 640 (or the support frame 642 thereof) on the housing 610. In some embodiments, the support component 640 (or the support frame 642 thereof) may be fixed on the housing 610 through the side edge 6424 and the fixing structure 650. Specifically, as described in connection with above, the fixing structure 650 may include the first plate 652 and the second plate 654. In some embodiments, two first plates 652 may be symmetrically disposed on the housing 610 and fixedly connected to two side edges 6424 of the support frame 642. Accordingly, the support component 640 (or the support frame 642 thereof) can be fixed on the housing 610.

In some embodiments, the noise reduction component 620 may include one or more noise reduction units. Accordingly, the noise reduction device 600 may include one or more fixing structures 650. For example, one fixing structure 650 may be configured to support one noise reduction unit. As another example, one fixing structure 650 may be configured to support a plurality of noise reduction units. Specifically for example, two adjacent noise reduction units may be connected in series through the second plate 654 of the fixing structure 650 (e.g., the second plate 654 may be mounted on the side edges 6424 corresponding to the two adjacent noise reduction units and configured to connect the two adjacent noise reduction units), and two first plates 652 of the fixing structure 650 may be disposed outside of the two adjacent noise reduction units.

Figure 8A:
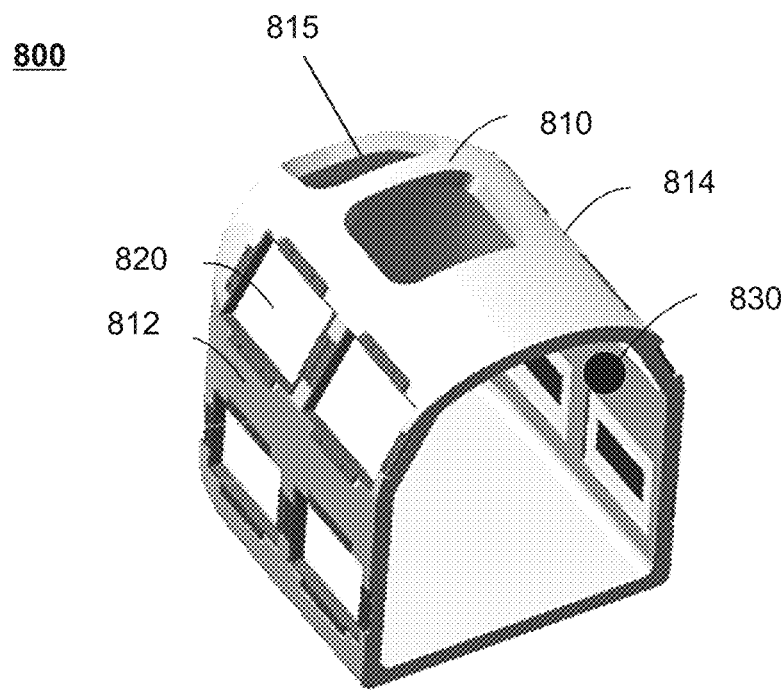
FIG. 8A is a schematic diagram illustrating an exemplary noise reduction device according to some embodiments of the present disclosure.

FIG. 8A is a schematic diagram illustrating an exemplary noise reduction device according to some embodiments of the present disclosure. A noise reduction device 800 may be an embodiment of the noise reduction device 160 described in FIG. 1.

In some embodiments, the noise reduction device 800 may be disposed on a medical device (e.g., the medical device 110). For illustration purposes, the medical device may be an MRI device or a head coil assembly of the MRI device.

As shown in FIG. 8A, the noise reduction device 800 may include a housing 810, a noise reduction component 820, and a noise receiving component 830.

The housing 810 may be configured to support and protect components of the noise reduction device 800. In some embodiments, the housing 810 may include a first side 812 and a second side 814 opposite to each other. In some embodiments, the housing 810 may also include a top surface and a bottom surface. In some embodiments, the housing 810 may also include a front end surface and a rear end surface. In some embodiments, the front end surface of the housing 810 may be closed, and the rear end surface of the housing 810 may be open.

In some embodiments, the housing 810 may form an accommodation chamber where a medical device can be located. In some embodiments, a window 815 may be disposed on the top surface of the housing 810. In some embodiments, the accommodation chamber may be entered through the window 815. In some embodiments, the window 815 may be used to enable a subject located in a head coil assembly of an MRI device or a support assembly of the medical device to communicate with the outside world. In some embodiments, there may be one or more windows on the housing 810, which is not intended to be limiting.

The noise reduction component 820 may be used for the noise reduction. In some embodiments, the noise reduction component 820 may generate sound information matching acoustic noise information received by the noise receiving component 830, realizing the noise reduction. More detailed descriptions of the noise reduction may be found elsewhere in the present disclosure and not repeated here. In some embodiments, the noise reduction component 820 may include a plurality of noise reduction units oppositely distributed on the first side 812 and the second side 814. For example, four noise reduction units are disposed on the first side 812 and four noise reduction units are symmetrically disposed on the second side 814. In some embodiments, the noise reduction units (e.g., the four noise reduction units) may be symmetrically disposed with respect to a center of the first side 812. Similarly, the noise reduction units (e.g., the four noise reduction units) may be symmetrically disposed with respect to a center of the second side 814. In some embodiments, the noise reduction component 820 may include a plurality of noise reduction units oppositely distributed on the top surface and the bottom surface of the housing 810. In some embodiments, the noise reduction component 820 may include a plurality of noise reduction units oppositely distributed on the front end surface and the rear end surface of the housing 810.

In some embodiments, the noise reduction component 820 may include a flat panel speaker or a curved speaker. For example, the noise reduction component 820 may be a ceramic piezoelectric flat panel speaker. Since the ceramic piezoelectric flat panel speaker generates no electromagnetic interference and/or radiation, the ceramic piezoelectric flat panel speaker may be used in medical devices with strong magnetic fields and high noise, for example, a head coil assembly of an MRI device, a support assembly of a medical device, etc.

The noise receiving component 830 may be configured to receive the acoustic noise information of the scanning environment where the medical device is located. In some embodiments, the noise receiving component 830 may include a microphone or other components that can receive the acoustic noise information. In some embodiments, the noise receiving component 830 may be disposed on an inner surface of the housing 810. In some embodiments, the noise receiving component 830 may be disposed with respect to the noise reduction component 820. For example, the noise receiving component 830 may be parallel to the noise reduction component 820. As another example, an angle may be between the noise receiving component 830 and the noise reduction component 820.

It should be noted that the noise reduction device 800 is provided for illustration purposes, and is not intended to limit the scope of the present disclosure. For persons having ordinary skills in the art, multiple variations and modifications may be made under the teachings of the present disclosure. However, those variations and modifications do not depart from the scope of the present disclosure. For example, the noise reduction device 800 (and/or the components thereof) may be the same as or similar to the noise reduction device 600, more descriptions can be found in FIGS. 6A-6D and the descriptions thereof.

Figure 8B:
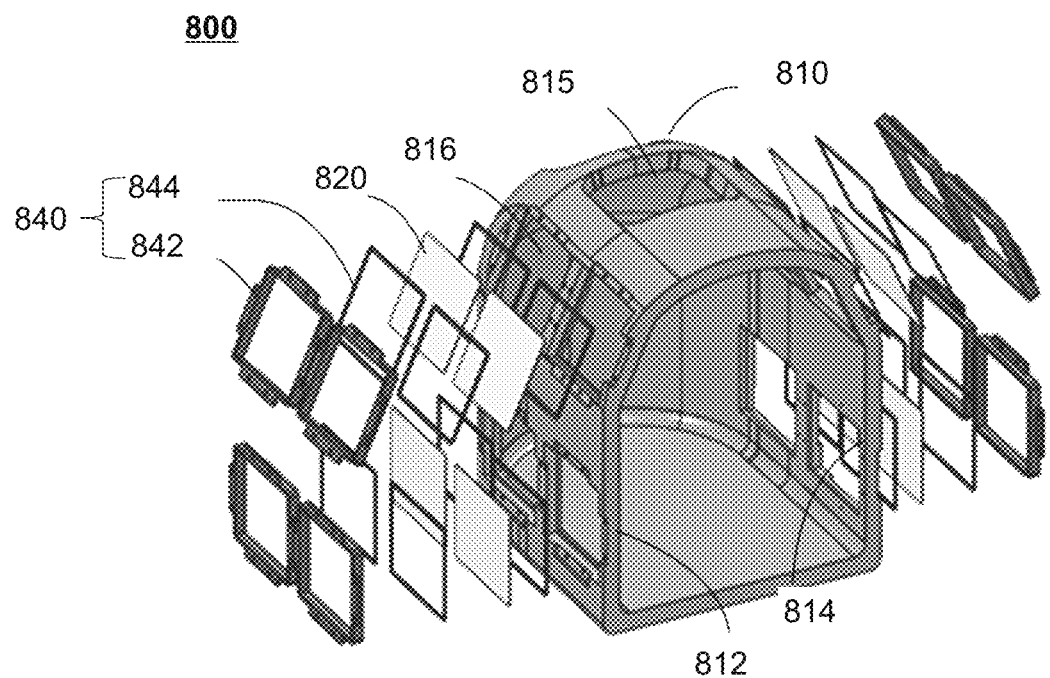
FIG. 8B is a schematic diagram illustrating an exemplary breakdown structure of an exemplary noise reduction device according to some embodiments of the present disclosure.

FIG. 8B is a schematic diagram illustrating an exemplary breakdown structure of an exemplary noise reduction device according to some embodiments of the present disclosure.

In some embodiments, at least one through hole (also referred to as "open") 816 may be disposed at a position of the housing 810 where the noise reduction component 820 is located. In some embodiments, the noise reduction component 820 (or the noise reduction units thereof) may be mounted through the open(s) 816. For example, the noise reduction component 820 (or the noise reduction units thereof) may be mounted through open(s) on the first side 812 and/or the second side 814. Accordingly, the noise reduction component 820 (or the noise reduction units thereof) may be disposed adjacent to the ears of the subject, thereby improving the performance of the noise reduction. As another example, the noise reduction component 820 (or the noise reduction units thereof) may be mounted through open(s) on the first side 812 and/or the second side 814 to match a shape of the housing 810. For instance, a portion of the noise reduction component 820 may be disposed parallel to a vertical direction, and a portion of the noise reduction component 820 may be dispose to form an angle with the vertical direction, so as to match a shape of the housing 810. In some embodiments, the at least one through hole 816 may be the same or similar to the at least one through hole 616, more descriptions can be found in FIGS. 6A-6D and the descriptions thereof.

In some embodiments, the noise reduction device 800 may also include a support component 840 including a support frame 842 and a vibration isolation structure 844. In some embodiments, the support frame 842 may be disposed on the open 816. The noise reduction component 820 (or the noise reduction unit(s) thereof) may be fixed on the housing 810 through the support frame 842. In some embodiments, the vibration isolation structure 844 may be disposed between the support frame 842 and the noise reduction component 820 (or the noise reduction unit(s) thereof). Additionally or alternatively, the vibration isolation structure 844 may be disposed between the housing 810 and the noise reduction component 820 (or the noise reduction unit(s) thereof). By disposing the vibration isolation structure 844, the vibrations of the noise reduction component 820 (or the noise reduction unit(s) thereof) on the housing 810 can be weakened through the vibration isolation structure 844 to avoid secondary noise. Further, the noise reduction component 820 (or the noise reduction unit(s) thereof) can be reliably fixed on the housing 810, which can generate a substantially ideal vibration mode, thereby improving the sound radiation performance. In some embodiments, the support component 840 may be the same as or similar to the support component 640, more descriptions can be found in FIGS. 6A-6D and the descriptions thereof.

Figure 9:
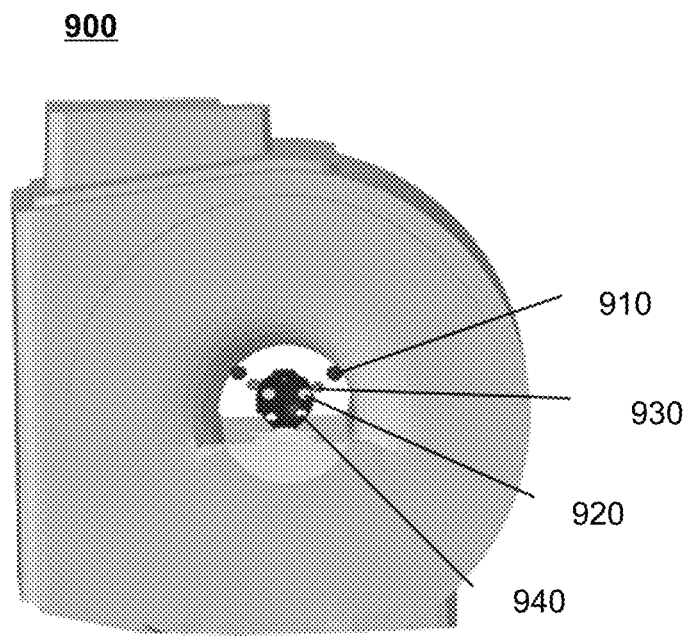
FIG. 9 is a schematic diagram illustrating an exemplary MRI device with a noise reduction device according to some embodiments of the present disclosure.

FIG. 9 is a schematic diagram illustrating an exemplary MRI device with a noise reduction device according to some embodiments of the present disclosure.

In some embodiments, an MRI device 900 may include a noise reduction device. Merely by way of example, the noise reduction device may be disposed on a head coil assembly of the MRI device 900.

As illustrated in FIG. 9, the noise reduction device may include a first noise receiving component 910 located on an inner side wall of a chamber (e.g., a scanning chamber of the MRI device 900), a first noise reduction component 920 located on an outer surface of a housing (e.g., an outer housing of the head coil assembly), a second noise receiving component 930 located on an inner surface of the housing, and a second noise reduction component 940 located on the inner surface of the housing. A processing component of the noise reduction device may be configured to control the first noise reduction component 920 to generate first sound information matching first acoustic noise information received by the first noise receiving component 910 and/or control the second noise reduction component 940 to generate second sound information matching second acoustic noise information received by the second noise receiving component 930, wherein the first acoustic noise information and the second acoustic noise information are from a scanning environment where the MRI device 900 is located. Accordingly, the first noise reduction component 920 and the first noise receiving component 910 may be used to eliminate noise in a low frequency band, and the second noise reduction component 940 and the second noise receiving component 930 may be used to eliminate noise in a middle frequency band.

Figure 10:
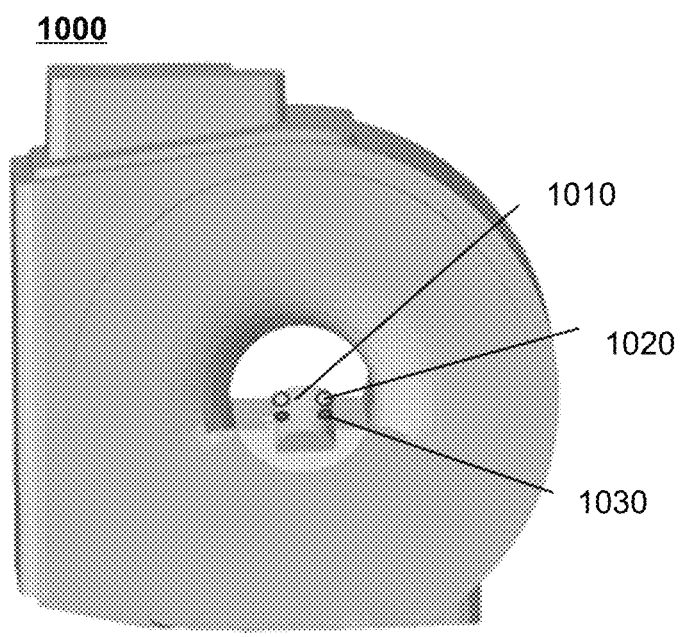
FIG. 10 is a schematic diagram illustrating an exemplary MRI device with a noise reduction device according to some embodiments of the present disclosure.

FIG. 10 is a schematic diagram illustrating an exemplary MRI device with a noise reduction device according to some embodiments of the present disclosure.

As described in connection with FIGS. 6A-6D and/or FIGS. 8A-8B, an MRI device disposed with a noise reduction device (e.g., the noise reduction device 600, the noise reduction device 800) may be used to perform an MRI scan on a child.

Merely by way of example, as illustrated in FIG. 10, an MRI device 1000 with a noise reduction device may be used to perform an MRI scan on a child (including a fetus in a pregnant woman's belly, a premature baby). The noise reduction device may include a housing 1010, a noise receiving component 1020, and a noise reduction component 1030. The housing 1010 may be used as a baby incubator to accommodate a baby. Alternatively, the housing 1010 may include an acoustic shield used as the baby incubator. In some embodiments, the housing 1010 may be placed on a table of the MRI device 1000, and may be moved into or out of a scanning chamber of the MRI device 1000. In some embodiments, the noise receiving component 1020 and the noise reduction component 1030 may be disposed in the housing 1010 (or the acoustic shield of the housing 1010).

By disposing the noise reduction device on the MRI device, the MRI scan can be performed on the children without headphones or other hearing protection components worn.

Figure 11:
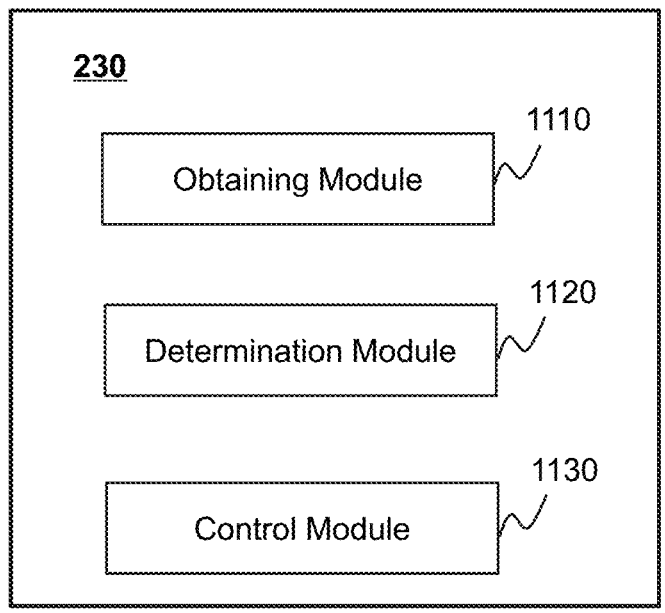
FIG. 11 is a block diagram illustrating an exemplary processing component according to some embodiments of the present disclosure.

FIG. 11 is a block diagram illustrating an exemplary processing component according to some embodiments of the present disclosure. In some embodiments, the modules illustrated in FIG. 11 may be implemented on a computing device. In some embodiments, the processing component 230 may include an obtaining module 1110, a determination module 1120, and a control module 1130.

The obtaining module 1110 may be configured to obtain acoustic noise information received by a noise receiving component (e.g., the noise receiving component 210). The acoustic noise information may refer to information of acoustic noise corresponding to a scanning environment where a medical device (e.g., the medical device 110) is located. More descriptions regarding the obtaining of the acoustic noise information may be found elsewhere in the present disclosure. See, e.g., operation 1202 and relevant descriptions thereof.

The determination module 1120 may be configured to determine sound information matching the acoustic noise information. The sound information may include parameter (s) (e.g., a frequency, an amplitude, a timber, a phase) of an anti-sound corresponding to the acoustic noise information. More descriptions regarding the determination of the sound information may be found elsewhere in the present disclosure. See, e.g., operation 1204 and relevant descriptions thereof.

The control module 1130 may be configured to control a noise reduction component (e.g., the noise reduction component 220) to generate the sound information. More descriptions regarding the control of the noise reduction component may be found elsewhere in the present disclosure. See, e.g., operation 1206 and relevant descriptions thereof.

The modules in the processing component 230 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above descriptions of the processing component 230 are provided for the purposes of illustration, and not intended to limit the scope of the present disclosure. For persons having ordinary skills in the art, various variations and modifications may be conducted under the guidance of the present disclosure. However, those variations and modifications do not depart from the scope of the present disclosure. In some embodiments, the processing component 230 may include one or more other modules. For example, the processing component 230 may include a storage module used to store data generated by the modules in the processing component 230. In some embodiments, two or more of the modules may be combined as a single module, and any one of the modules may be divided into two or more units.

Figure 12:
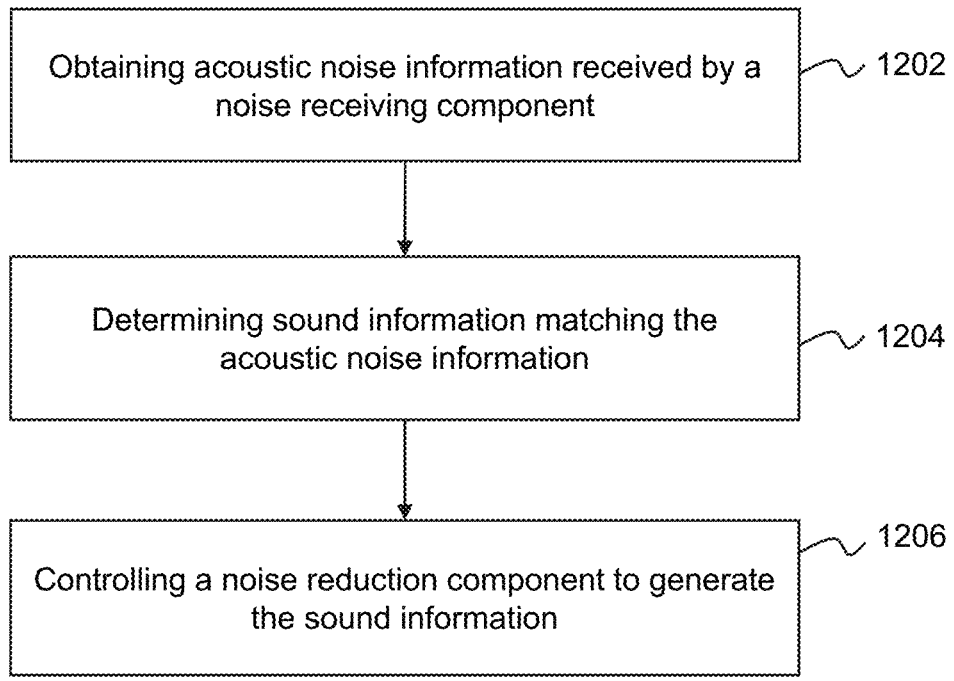
FIG. 12 is a flowchart illustrating an exemplary process for noise reduction according to some embodiments of the present disclosure.

FIG. 12 is a flowchart illustrating an exemplary process for noise reduction according to some embodiments of the present disclosure. In some embodiments, process 1200 may be executed by the medical system 100. For example, the process 1200 may be stored in the storage device 150 in the form of instructions (e.g., an application), and invoked and/or executed by the processing device 140 or the processing component 230. The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1202, the processing component 230 (e.g., the obtaining module 1110) may obtain acoustic noise information received by a noise receiving component (e.g., the noise receiving component 210).

The acoustic noise information may refer to information of acoustic noise corresponding to a scanning environment where a medical device (e.g., the medical device 110) is located. In some embodiments, the acoustic noise information may include parameter(s) (e.g., a frequency, an amplitude, a timber, a phase) of the acoustic noise.

In some embodiments, the processing component 230 may obtain the acoustic noise information from the noise receiving component 210 or a storage device (e.g., the storage device 150) that stores the acoustic noise information.

In 1204, the processing component 230 (e.g., the determination module 1120) may determine sound information matching the acoustic noise information.

The sound information may include parameter(s) (e.g., a frequency, an amplitude, a timber, a phase) of an anti-sound corresponding to the acoustic noise information. For example, the amplitude of the anti-sound may be the same as or substantially the same as the amplitude of the acoustic noise information; the phase of the anti-sound may be opposite to or substantially opposite to the phase of the acoustic noise information. In some embodiments, the sound information may counteract the acoustic noise information, thereby realizing the noise reduction.

In some embodiments, the processing component 230 may determine the sound information matching the acoustic noise information based on a signal processing model (e.g., the signal processing model 300). More descriptions of the signal processing model may be found elsewhere in the present disclosure (e.g., FIG. 3 and the descriptions thereof).

In 1206, the processing component 230 may (e.g., the determination module 304) may control a noise reduction component (e.g., the noise reduction component 220) to generate the sound information.

For example, the processing component 230 may generate a control instruction including the sound information, and transmit the control instruction including the sound information to the noise reduction component. Accordingly, the noise reduction component may generate the sound information based on the control instruction.

Some embodiments of the present disclosure provide a noise reduction device that can generate the sound information matching the acoustic noise information. The sound information may counteract the acoustic noise information, thereby realizing the noise reduction.

It should be noted that the description of the process 1200 is provided for the purposes of illustration, and is not intended to limit the scope of the present disclosure. For persons having ordinary skills in the art, various variations and modifications may be conducted under the teaching of the present disclosure. For example, an additional operation for checking the sound information may be added after operation 1204. However, those variations and modifications may not depart from the protection of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, device, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A device for noise reduction, comprising:
    a noise receiving component configured to receive acoustic noise information of a scanning environment where a medical device is located;
    a noise reduction component;
    a processing component configured to control the noise reduction component to generate sound information matching the acoustic noise information received by the noise receiving component;
    a support component configured to support the noise reduction component, wherein the support component includes a support frame and a vibration isolation structure, the vibration isolation structure is located in the support frame or located between the support frame and the noise reduction component; and
    a housing configured to support the noise receiving component and the noise reduction component.

2. The device of claim 1, wherein
    the noise receiving component is located on an inner surface or an outer surface of the housing, and
    the noise reduction component is located on the outer surface of the housing.

3. The device of claim 1, wherein the noise reduction component includes a flat panel speaker or a curved speaker.

4. The device of claim 1, wherein a parameter of the noise reduction component is designed according to noise reduction requirement, the parameter including at least one of a shape, a length, a width, a radius, or a thickness of the noise reduction component.

5. The device of claim 1, wherein the noise reduction component includes at least two noise reduction units, the at least two noise reduction units being disposed on two opposite sides of the housing.

6. The device of claim 1, wherein the noise reduction component includes at least two noise reduction units, wherein
parameters of the at least two noise reduction units are at least partially different, the parameter of the noise reduction unit including at least one of a shape, a length, a width, a radius, or a thickness.

7. The device of claim 1, wherein at least one through hole is disposed at a position of the housing where the noise reduction component is located.

8. The device of claim 7, wherein the at least one through hole is disposed in rows and columns.

9. The device of claim 7, wherein a size of the at least one through hole is within a preset range.

10. The device of claim 1, wherein the support frame includes a frame body and a side edge, wherein
the side edge is disposed on the frame body and protrudes from the frame body.

11. The device of claim 10, further comprising:
a fixing structure fixedly connected to the side edge.

12. The device of claim 1, further comprising:
a second housing located outside the housing, wherein the second housing and the housing form an enclosed structure.

13. A device for noise reduction disposed on a head coil assembly, comprising:
a noise receiving component configured to receive acoustic noise information of a scanning environment where a medical device is located;
a first housing;
a second housing, the second housing and the first housing forming an accommodation chamber;
a noise reduction component located on the first housing and/or the second housing;
a support component configured to support the noise reduction component, wherein the support component includes a support frame and a vibration isolation structure, the vibration isolation structure is located in the support frame or located between the support frame and the noise reduction component; and
a processing component configured to control the noise reduction component to generate sound information matching the acoustic noise information received by the noise receiving component.

14. The device of claim 13, wherein the noise reduction component includes a flat panel speaker or a curved speaker.

15. The device of claim 13, wherein the noise reduction component includes at least two noise reduction units, parameters of the at least two noise reduction units are at least partially different, the parameter of the noise reduction unit including at least one of a shape, a length, a width, a radius, or a thickness.

16. The device of claim 13, wherein the support frame includes a frame body and a side edge, the side edge is disposed on the frame body and protrudes from the frame body.

17. A device for noise reduction, comprising:
a first noise receiving component located on an inner side wall of a chamber;
a first noise reduction component located on an outer surface of a housing;
a second noise receiving component located on an inner surface of the housing;
a second noise reduction component located on the inner surface of the housing;
a support component configured to support a noise reduction component, wherein the noise reduction component includes the first noise receiving component, the first noise reduction component, the second noise receiving component and the second noise reduction component, the support component includes a support frame and a vibration isolation structure, the vibration isolation structure is located in the support frame or located between the support frame and the noise reduction component; and
a processing component configured to control the first noise reduction component to generate first sound information matching first acoustic noise information received by the first noise receiving component and/or control the second noise reduction component to generate second sound information matching second acoustic noise information received by the second noise receiving component, wherein the first acoustic noise information and the second acoustic noise information are from a scanning environment where a medical device is located.

18. The device of claim 17, wherein at least one of the first noise reduction component or the second noise reduction component includes a flat panel speaker or a curved speaker.

19. The device of claim 17, wherein at least one of the first noise reduction component or the second noise reduction component includes at least two noise reduction units, the at least two noise reduction units being disposed on two opposite sides of the housing.

20. The device of claim 17, further comprising:
a fixing structure fixedly connected to a side edge of the support frame.

* * * * *